US010980588B2

(12) United States Patent
Nieber et al.

(10) Patent No.: US 10,980,588 B2
(45) Date of Patent: Apr. 20, 2021

(54) MODULAR DISCHARGE DEVICE WITH SEPARATOR ELEMENT

(71) Applicant: SULZER MIXPAC AG, Haag (CH)

(72) Inventors: Benjamin Nieber, Eschenbach (CH); Martin Veid, Weggis (CH); Beat Mathys, Muri (CH); Stefan Kugler, Zürich (CH)

(73) Assignee: Sulzer Mixpac AG, Haag (CH)

( * ) Notice: Subject to any disclaimer, the term of this patent is extended or adjusted under 35 U.S.C. 154(b) by 89 days.

(21) Appl. No.: 16/344,185

(22) PCT Filed: Oct. 3, 2017

(86) PCT No.: PCT/EP2017/075061
§ 371 (c)(1),
(2) Date: Apr. 23, 2019

(87) PCT Pub. No.: WO2018/077575
PCT Pub. Date: May 3, 2018

(65) Prior Publication Data
US 2019/0254726 A1    Aug. 22, 2019

(30) Foreign Application Priority Data

Oct. 24, 2016   (CH) .................................... 01417/16
Mar. 13, 2017   (CH) .................................... 00298/17

(51) Int. Cl.
*A61B 17/58*       (2006.01)
*A61B 17/60*       (2006.01)
(Continued)

(52) U.S. Cl.
CPC ...... *A61B 17/8811* (2013.01); *A61B 17/8825* (2013.01); *A61B 17/8827* (2013.01);
(Continued)

(58) Field of Classification Search
CPC combination set(s) only.
See application file for complete search history.

(56) References Cited

U.S. PATENT DOCUMENTS

2004/0087906 A1    5/2004   Henderson et al.
2006/0264964 A1    11/2006  Scifert et al.
(Continued)

FOREIGN PATENT DOCUMENTS

DE    102 47 963 A1    5/2004
EP    0 470 393 A1     2/1992
(Continued)

OTHER PUBLICATIONS

International Search Report for PCT/EP2017/075061 dated Jan. 17, 2018 [PCT/ISA/210].

*Primary Examiner* — Sameh R Boles
(74) *Attorney, Agent, or Firm* — Sughrue Mion, PLLC

(57) ABSTRACT

A separator element (300) is designed to prevent the passage of granulate along an axial direction (L) but to allow the passage of liquid along the axial direction (L). The separator element (300) has an internal thread (310) open towards its proximal end, and an external thread (320) open towards the distal end. At its proximal end, the separator element additionally has at least one resilient locking arm (330) which is arranged on the outer circumference and winch extends with its free end in the proximal direction. In this way, the separator element can be mounted on the discharge opening of a container (100) and, by means of a closure piece (400), can be fixed on the container in such a way that the separator element remains on the container when the closure piece is removed.

24 Claims, 16 Drawing Sheets

(51) Int. Cl.
    *A61F 2/00*          (2006.01)
    *A61B 17/88*        (2006.01)
    *A61C 5/62*          (2017.01)
    *A61M 39/10*       (2006.01)
    *A61F 2/46*          (2006.01)
    *A61M 5/31*          (2006.01)

(52) U.S. Cl.
    CPC ............ *A61C 5/62* (2017.02); *A61M 39/1055* (2013.01); *A61B 2017/8838* (2013.01); *A61F 2/4601* (2013.01); *A61M 2005/3104* (2013.01)

(56) References Cited

U.S. PATENT DOCUMENTS

2012/0083790 A1*   4/2012   Dubach .............. A61B 17/8811
                                                         606/94
2015/0045768 A1    2/2015   Schmieding et al.

FOREIGN PATENT DOCUMENTS

| EP | 1 093 767 A1 | 4/2001 |
| EP | 2 436 342 A1 | 4/2012 |
| EP | 3 042 679 A1 | 7/2016 |

* cited by examiner

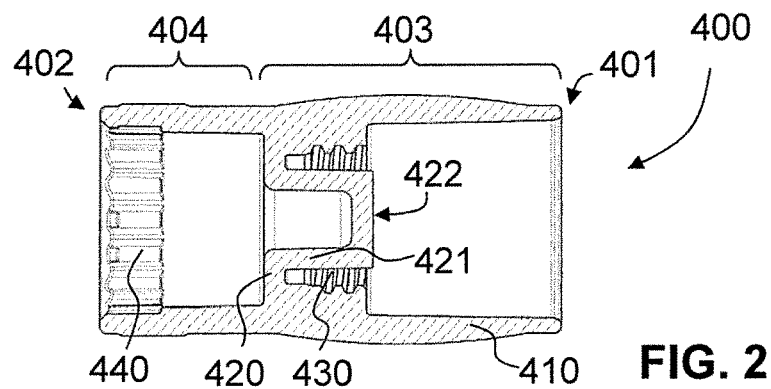
FIG. 21
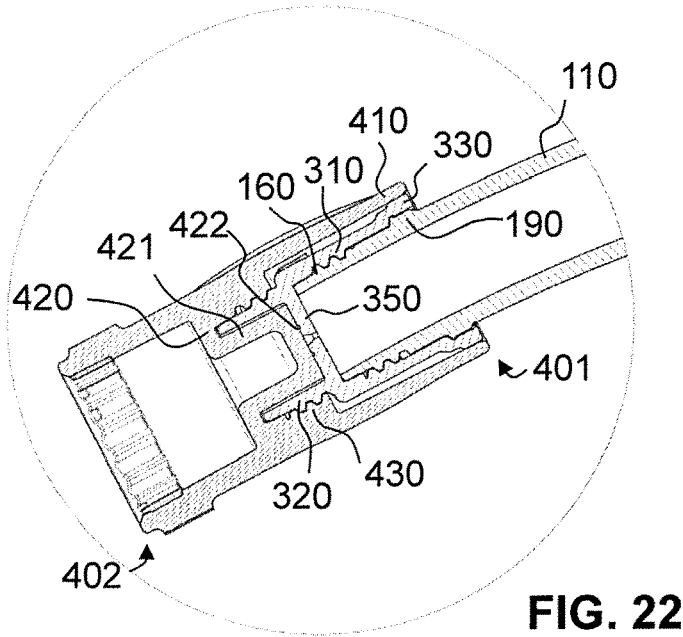
FIG. 22
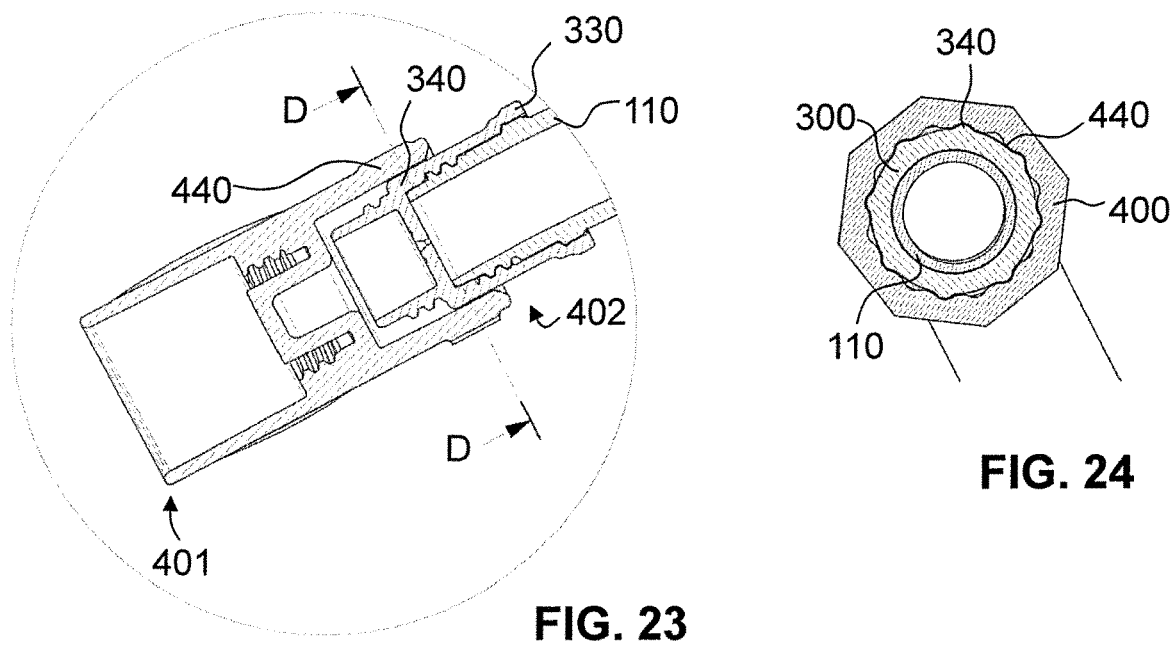
FIG. 23
FIG. 24

MODULAR DISCHARGE DEVICE WITH SEPARATOR ELEMENT

CROSS REFERENCE TO RELATED APPLICATIONS

This application is a National Stage of International Application No. PCT/EP2017/075061, filed on Oct. 3, 2017, which claims priority from Swiss Patent Application No. 01417/16, filed on Oct. 24, 2016, and Swiss Patent Application No. 00298/17, filed on Mar. 13, 2017.

TECHNICAL FIELD

The present invention relates to separator elements which are configured to prevent the passage of a granulate but to permit the passage of liquid, discharge devices which are specifically designed to be used with such separator elements and methods for handling such discharge devices.

PRIOR ART

In different medical fields such as dentistry, orthopedics or reconstructive surgery, bone graft materials are used. The bone graft material generally consists of a granulate of natural or synthetic origin (for example a two-phase calcium phosphate/hydroxyapatite material) and a liquid (for example endogenous blood or a physiological saline solution).

Generally, the granulate is provided in a tray and the liquid phase is added, whereby the granulate is wetted. In order to apply the bone graft material thus produced onto the patient, it is brought to the intended point of use by a spatula. Depending on the location of the intended point of use, this may be difficult or even impossible and since the material is loose and heaped up on the spatula there is the risk that the material may slip from the spatula when supplied. Additionally, such handling is time-consuming.

In the prior art, therefore, it has been proposed to receive the granulate in a syringe and to wet the granulate with the liquid directly in the syringe. In order to hold back the granulate in the syringe, but to permit the liquid to be received in the syringe, it is known to provide a filter or a sieve on the syringe.

Thus a granulate syringe is disclosed in EP 0 470 393 B1 in which a cap with a disk made of porous material is applied or screwed onto the outlet end of the syringe housing. In order to discharge the mixture, the cap is removed and a piston is pushed forward.

EP 1 093 767 B1 discloses a syringe with a syringe cylinder which is filled with granulate. A cannula tip is attached by means of a friction fit to the cylinder, said cannula tip having a sieve in a recess. Blood is suctioned into the syringe cylinder via an opening. Once the blood is mixed sufficiently with the granulate, the cannula tip is manually pushed down from the syringe cylinder.

A syringe for the application of bone graft material which has a cylinder in which granulate is received is disclosed in EP 2 436 342 B1. The cylinder has at its distal end an external thread, a removable attachment with an internal thread being held thereon. The attachment has an injection opening and drainage openings. Liquid is injected through the injection opening into the cylinder in order to wet and soak the granulate and excess liquid is then forced out again through the drainage openings. Once the bone graft material is sufficiently wetted with liquid, the attachment is unscrewed and replaced by a curved discharge nozzle.

In such syringes, however, there is a need for further improvement with regard to handling.

SUMMARY OF THE INVENTION

In a first aspect, the present invention provides a separator element.

The separator element defines a proximal end and a distal end. The separator element comprises a filter region which is configured to prevent the passage of a granulate in an axial direction but to permit the passage of liquid in the axial direction. The separator element also comprises an internal thread which is open toward the proximal end and which extends around the axial direction and comprises at least one resilient locking arm which is arranged on the outer periphery, which is configured in the region of the proximal end of the separator element and which extends with its free end in the proximal direction toward the proximal end.

The term "thread" is to be understood broadly here. It encompasses any connecting structures by means of which two parts are able to be brought into engagement increasingly guided by a combined rotational and axial movement. In particular, structures such as those required for producing a bayonet connection also come within this term. The "direction" of the thread is denoted as the direction of the rotational component of the engagement movement. The threads specified in this document may, in particular, be threads in the narrower conventional sense, i.e. single-start or multi-start threads with one or more helical thread pitches.

The separator element may be screwed by means of its internal thread onto a suitable external thread in the region of a discharge opening of a container. Moreover, a closure may be attached to the separator element. To this end, the separator element at its distal end may also have a suitable connecting structure, for example an external thread which is open toward the distal end (in the above-defined broad sense) and which also extends coaxially to the internal thread in the axial direction.

In order to prevent the closure from entraining the separator element when the closure is removed from the separator element, the separator element has the at least one resilient locking arm. The at least one locking arm serves to create a locking engagement with the container in order to secure the separator element to the container when the closure is removed from the separator element. Preferably, this locking engagement is only releasable after the closure has been at least partially removed from the separator element, i.e. the locking arm is preferably arranged such that the closure is able to block a radial deflection of the locking arm outwardly when it is attached to the separator element.

Preferably, two or more such locking arms which are arranged so as to be distributed over the periphery of the separator element are present in order to ensure a securing of the separator element on the container which is as uniform as possible. It should be mentioned that statements which are made hereinafter about an individual locking arm apply equally to each further locking arm in the case of a plurality of locking arms, and that statements which relate to a plurality of locking arms apply even if only one individual locking arm is present.

The filter region of the separator element serves to hold back a granulate (for example a component of a bone graft material) in the container but to permit the receiving of liquid in the container. The filter region may be configured, for example, as a sieve plate with a plurality of axial through-openings. Alternatively, the filter region may also be formed, for example, from a porous material which forms a network of channels connected together. In this manner the separator element permits a liquid, for example blood or saline solution, to be suctioned or injected into the container, without a granulate received in the container, in particular for a bone graft material, being able to escape from the container. Preferably, the filter region, the internal thread and the spring arms and optionally the external thread are configured integrally with one another.

In some embodiments, the filter region extends as far as the distal end of the separator element. In this case, therefore, the distal end of the filter region also forms the distal end of the separator element as a whole. This facilitates the receiving of a liquid from a tray or a recess in a manner which is as complete as possible. The external thread, if present, in this case may surround the filter region, i.e. may be configured on the radial outer face of the filter region.

Such an embodiment, however, may be problematical in terms of production technology. In other embodiments, therefore, the external thread is configured on a pipe connector which in the distal direction adjoins the filter region. The pipe connector thus defines a cavity on the inside, wherein the cavity is delimited in the proximal direction by the filter region. This is advantageous in terms of production technology, since for the unmolding of the thread a simple rotatable core may be used.

Preferably, the separator element has a rotationally symmetrical basic shape relative to rotations about a central longitudinal axis which extends in the axial direction.

The at least one locking arm preferably has a rear-engagement element in the region of its free end on the inner face. This rear-engagement element serves to engage behind a complementary structure on the container in order to secure in this manner the separator element to the container. The rear-engagement element may, in particular, take the form of a radially inwardly extending locking lug.

Alternatively or additionally, the at least one locking arm in the region of its free end on the inner face may have an engagement structure which is configured to cooperate with a rotational locking structure on the container. In this manner, a rotational securing may also be achieved as an alternative or in addition to an axial securing. The engagement structure may be configured, in particular, in the form of a toothing on the inner face, which extends around the axial direction.

In order to enable the closure to be able to block radial deflections of the locking arm outwardly, it is advantageous if the at least one locking arm is configured on the separator element in a region of the outer periphery of the separator element, such that an outer surface of the at least one locking arm is arranged flush with an outer surface of the separator element located distally from the locking arm, or is arranged offset radially outwardly. In particular, it is advantageous if the at least one locking arm defines the maximum radius of the separator element transversely to the axial direction. As a result, the outer wall of a closure may easily come to rest on the outer surface of the locking arm in order to block the locking arm and optionally press it radially inward.

The locking arms advantageously extend as far as a region located proximally from the internal thread of the separator element in the axial direction. In this case, the locking arms may adjoin the internal thread in the proximal direction. The internal thread, however, may also be at least partially configured on the inner face of the locking arms.

One or more driver elements may be configured on the separator element on the outer face in order to permit a positive engagement of the separator element with a driver in the peripheral direction. As a result, the separator element may be easily unscrewed from the container. The driver elements, for example, may take the form of radially protruding, axially extending longitudinal ribs distributed over the periphery. In particular, the driver elements may form a toothing in the peripheral direction.

Preferably, the driver elements are arranged proximally from the external thread and distally from the locking arms on the separator element. However, such driver elements are also advantageous if the separator element has no locking arms.

A discharge device is produced by combining a separator element of the type described above with a container. In this case the container serves for receiving a product and may be designed as follows: with a peripheral container wall, a proximal container end, a distal container end and a discharge opening on the distal container end, wherein in the region of the distal container end an external thread which extends around the axial direction is configured on the container wall, and wherein the external thread of the container is able to be brought into engagement with the internal thread of the separator element in order to attach the separator element to the distal container end. The container may be prefilled with the aforementioned granulate, in particular a component of a bone graft material.

The discharge device may also have a feed element with a piston and piston rod, in order to discharge the product received in the container through the discharge opening from the container after removing the separator element. The piston may bear sealingly against the inner face of the container wall, additionally in order to permit liquid to be suctioned through the separator element into the container.

An axial locking structure may be configured proximally from the external thread of the container on the outer face on the container wall, wherein the at least one locking arm of the separator element is able to be brought into engagement with the axial locking structure such that it impedes or even fully blocks a proximal movement of the separator element relative to the container (in particular by an axial positive connection) and wherein the locking arm is able to be brought out of engagement with the axial locking structure by an outward radial deflection of the locking arm. In particular, the locking arm may axially engage with its aforementioned rear-engagement element behind the axial locking structure in order to produce an axial positive connection in this manner.

The axial locking structure, for example, may comprise an annular bead, the at least one locking arm being able to be brought thereby into locking engagement in a resilient manner. Alternatively, however, a step or an annular groove which slopes down in the proximal direction may also be configured in the container wall, for example.

Alternatively or additionally to the axial locking structure, a rotational locking structure may be configured proximally from the external thread of the container on the outer face on the container wall. A complementary engagement structure is configured on at least one locking arm of the separator element, said engagement structure being able to be brought into engagement with the rotational locking structure, such that it impedes a rotation of the separator element relative to the container, and being able to be brought out of engagement by an outwardly oriented radial deflection of the locking arm. The engagement structure may be identical to the rear-engagement element, i.e. the rear-engagement element may effect both an axial securing and a rotational securing of the separator element on the container.

The rotational locking structure is preferably arranged proximally from the axial locking structure on the container wall. However, it may also be configured together with the axial locking structure in the same region of the container wall. If, for example, the axial locking structure is an annular bead, this may be interrupted at a few points in order to permit the axially secured and rotationally secured engagement of a correspondingly designed engagement structure on the locking arm.

The rotational locking structure may be configured, in particular, as an external toothing which extends at least over a part of the periphery of the container wall. The complementary engagement structure may be configured as an internal toothing on the inner face of the locking arms.

In order to close the separator element in the distal direction, the discharge device may be provided with the aforementioned closure. This closure preferably has a peripheral outer wall, a proximal closure end, a distal closure end and a top wall. The closure may be attached to the separator element in a closing position. The top wall of the closure axially covers the distal end of the separator element in the closing position. In order to secure the separator element in an improved manner to the container, the outer wall of the closure preferably radially covers the at least one locking arm in the closing position such that the outer wall impedes a radial deflection of the locking arm or even deflects the locking arm from its unloaded position inwardly toward the container wall.

An internal thread which is open toward the proximal closure end may be configured in the outer wall of the closure, said internal thread extending in the axial direction and the aforementioned external thread may be configured on the separator element. In the closing position, therefore, the external thread of the separator element is in engagement with the internal thread of the closure. The internal thread may be arranged, in particular, in a region of the outer wall between the proximal closure end and the top wall.

If the external thread of the separator element is configured on a pipe connector which defines a cavity on the inside, as has been described above, it is advantageous if a plug is configured on the top wall of the closure, said plug extending in the interior of the closure in the direction of the proximal closure end. Therefore, in the closing position this plug extends into the cavity, preferably such that in the closing position a proximal front face of the plug bears against the filter region. As a result, material from the interior of the container is prevented from being able to enter the cavity through the filter region as long as the closure is attached to the separator element. The internal thread may thus be at least partially configured in a region of the outer wall surrounding the plug.

In some applications it may be desirable to use the same closure even if a separator element is not present. The closure thus serves to close the container directly. Thus, for example, it may be desired to reattach the closure to the container after the granulate has been wetted in the container with liquid and the separator element has been removed. Of particular interest, however, is in applications in which from the start a granulate to be wetted is not received in the container but a ready-to-use mass (for example so-called "putty") which no longer needs to be mixed with a liquid before discharge. The mass may, in particular, be a bone graft material.

In this case, it is a drawback if the closure has a plug since this plug would protrude into the container when attaching the closure and would penetrate the material present in the distal end region of the container. Thus, in a development, it is proposed to design the closure as follows: the top wall forms a distal front face on the rear face of the plug and the closure between the distal front face and the distal closure end has a second internal thread which is open toward the distal closure end, which extends around the axial direction and which is configured in a complementary manner to the external thread on the distal container end. As a result, the closure with the second internal thread may be screwed in a reverse orientation relative to the closing position onto the external thread at the distal container end such that the distal front face covers the distal container end. The distal front face may be of any design, in particular planar, over the entire clear cross section of the closure so that in this orientation no component of the closure protrudes into the container interior when the closure is attached to the container. The second internal thread may, in particular, be of the same dimensions (in particular have the same thread number and pitch height) as the first internal thread.

Preferably, the outer wall of the closure in the closing position extends in the proximal direction at least as far as the proximal end of the separator element so that the closure entirely covers the separator element in the closing position. In this manner it is ensured that the separator element is not able to be inadvertently touched and thereby soiled, or that conversely a user is not able to be contaminated by material adhering to the separator element.

In order to wet the granulate received in the container with liquid, initially it is necessary to remove the closure. In this case, the locking arms on the separator element together with the outer wall of the closure ensure that the separator element remains on the container and is not inadvertently removed together with the closure. The addition of liquid takes place subsequently through the filter region of the separator element by suctioning or injecting.

After the liquid has been received in the container and mixed with the granulate present in the container, the separator element is removed from the container in order to discharge the finished product through the discharge opening. In order to simplify this process, the outer wall of the closure in the region of the distal closure end may have one or more drivers distally from the top wall on the inner face. The drivers are thus able to be brought into engagement with the driver elements of the separator element by the closure being connected to the separator element, in particular pushed thereon, in a reverse orientation relative to the closing position in the axial direction so that the separator element is able to be unscrewed from the container by means of the closure.

Such an embodiment is advantageous even if the separator element has no resilient locking arms. In this regard, a separator element with a proximal end and a distal end is also disclosed, comprising:

a filter region which is configured to prevent the passage of a granulate in an axial direction between the proximal end and the distal end but to permit the passage of liquid in the axial direction;

an internal thread which is open toward the proximal end and which extends around the axial direction; and one or more driver elements which are configured on the outer face on the separator element in order to permit a positive engagement of the separator element with a driver of a closure in the peripheral direction.

The driver elements, as already explained, may form a toothing in the peripheral direction.

The separator element, as already explained, may advantageously have an external thread which is open toward the distal end and which extends around the axial direction in order to screw on a closure. The external thread may be configured, in particular, on a pipe connector which on the inside defines a cavity, wherein the cavity is delimited in the proximal direction by the filter region.

Moreover, a discharge device is disclosed, said discharge device having a separator element of the type mentioned above with the aforementioned driver elements, wherein the aforementioned locking arms are optional. The discharge device also has one or more of the following features:

a container for receiving a product with a peripheral container wall, a distal container end and a discharge opening on the distal container end; and a closure with a peripheral outer wall, a proximal closure end, a distal closure end and a top wall.

An external thread which extends around the axial direction may be configured on the container wall in the region of the distal container end, wherein this external thread of the container is able to be brought into engagement with the internal thread of the separator element in order to attach the separator element to the distal container end. The closure is able to be attached to the separator element such that in a closing position the top wall of the closure axially covers the distal end of the separator element. The outer wall of the closure may have one or more drivers distally from the top wall on the inner face. The drivers may be brought into engagement with the driver elements of the separator element by the closure being connected to the separator element, in particular pushed thereon, in a reverse orientation relative to the closing position in the axial direction, so that the separator element is able to be unscrewed from the container by means of the closure.

The drivers and the driver elements may be brought into engagement with one another such that relative to the peripheral direction they create a positive connection with one another. The drivers may also comprise, for example, longitudinal ribs or cams and to this end the driver elements may comprise complementary longitudinal grooves or vice-versa. Additionally, the drivers and driver elements may also create an axially secured connection, for example by a frictional connection, by a snap connection, by a bayonet connection, etc. In the case of driver elements in the form of longitudinal grooves, for example, in each case a short transverse groove may adjoin the proximal end of these longitudinal grooves in order to permit a bayonet connection with the cam-shaped drivers. Thus it may be ensured that the closure and the separator element form a unit when removed from the container and the separator element does not fall out of the closure after removal. At the same time, the user is prevented from ever having to touch the separator element. A contamination between the user and the separator element is thus avoided in both directions.

A method for producing and for discharging a product with a discharge device of the type mentioned above is also disclosed, wherein the method comprises:

providing the discharge device in a state in which the container is filled with a granulate, the separator element is attached over the discharge opening of the container and the closure is attached to the separator element in the closing position, removing the closure from the separator element whilst the separator element remains on the container;

receiving a liquid through the separator element into the container in order to wet the granulate with the liquid and thus to produce a product which is ready for discharge;

connecting the closure to the separator element in a reverse orientation relative to the closing position, in particular by pushing the closure onto the separator element;

unscrewing the separator element from the container by means of the closure; and discharging the product which is ready for discharge through the discharge opening of the container.

As explained above, it may also be desired to prefill the container already from the start with a product which is ready for discharge, in particular a bone graft material. The separator element may then be entirely dispensed with. In order to ensure that optionally the closure may also be screwed directly onto the container, the external thread of the separator element and the external thread of the container preferably may be of the same dimensions so that the closure is optionally able to be screwed with its internal thread onto the separator element or directly onto the container. In other words, the internal thread of the closure optionally may be able to be brought into engagement with the external thread of the separator element or the external thread of the container.

In this case, generally a radial intermediate space is produced between the container wall and the outer wall of the closure if the closure is directly screwed onto the container. This intermediate space is produced, in particular, in a region located proximally from the thread. In order to prevent dirt from entering this intermediate space a bridging structure, preferably in the form of an annular bead, may be configured on the container wall on the outer face proximally from the external thread, said bridging structure protruding sufficiently far radially that it bridges the radial intermediate space. This bridging structure is, in particular, preferably arranged proximally from the axial locking structure and/or rotational locking structure.

The same container and the same closure may thus optionally be used without any structural alteration, with or without a separator element. This contributes to substantial cost savings since during the production of the container and the closure the same injection molds may be used irrespective of whether a separator element is provided. The container and closure in this case are thus effectively designed for use with a separator element even if this separator element is not required.

Accordingly, therefore, a discharge device is also disclosed, comprising a container for receiving a product with a peripheral container wall, a proximal container end, a distal container end and a discharge opening on the distal container end; and a closure with a peripheral outer wall, a proximal closure end, a distal closure end and a top wall, wherein an external thread which extends around an axial direction is configured on the container wall in the region of the distal container end, wherein an internal thread which extends around the axial direction is configured in the outer wall in a region located between the proximal closure end and the top wall, wherein the external thread of the container is in engagement with the internal thread of the closure, wherein the top wall of the closure covers the discharge opening of the container, wherein a radial intermediate space is present between the container wall and the outer wall of the closure, and wherein a bridging structure, preferably in the form of an annular bead, is configured on the container wall on the outer face proximally from the external thread, said bridging structure protruding sufficiently far radially that it bridges the radial intermediate space in order to prevent the entry of debris into the radial intermediate space.

In particular, the aforementioned axial locking structure and/or rotational locking structure may be configured on the outer wall on the outer face and the bridging structure is then preferably arranged proximally from the axial locking structure and/or rotational locking structure on the container wall as has already been described above.

Preferably, the bridging structure directly adjoins the proximal closure end or is entirely covered by the outer wall of the closure and the outer wall of the closure may bear against the bridging structure. This may take place in a sealed or non-sealed manner.

Generally, the container may have a first finger support on the outer face at the proximal container end. This serves as a proximal support for the index finger and middle finger if the user grips the container between the index finger and middle finger and with the thumb pushes forward the feed element in the distal direction out of the container. The feed element may have a thumb ring in order to permit not only such a distal feed movement but also to permit the feed element to be retracted using the thumb. In this case, in order to prevent the index finger and middle finger from slipping, the container may have a second finger support distally from the first finger support on the outer face, so that the fingers of a user are impeded from slipping in the distal direction.

Also disclosed is a closure which defines an axial direction, a proximal closure end and a distal closure end. The closure comprises:
  an outer wall circulating around the axial direction;
  a top wall which forms a distal front face;
  a plug which extends in the interior of the closure starting from the top wall in the proximal direction, wherein the plug forms a proximal front face at its free proximal end,
  a first internal thread which extends around the axial direction and is open toward the proximal closure end, and
  a second internal thread which is configured in a region located between the distal front face and the distal closure end, which extends around the axial direction and which is open toward the distal closure end.

As has already been described above, such a closure may optionally be used to be applied onto a separator element in a first orientation by means of the first internal thread, said separator element having distally from the filter region a pipe connector with an external thread, or said closure may be used in a second orientation to be attached directly to a prefilled container without the plug penetrating the material present in the container.

The first internal thread is preferably configured at least partially in a region of the outer wall surrounding the plug, so that it may be engaged in an external thread on the pipe connector.

As has already been explained in more detail above, the outer wall may have on the inner face one or more drivers distally from the distal front face, in particular in the region of the distal closure end, in order to permit the unscrewing of the separator element.

It is also proposed to accommodate the discharge device in a specific packaging which provides one or more further additional functions. In particular, it is proposed to provide a combination of a discharge device of the type mentioned above with a packaging receiving the discharge device. The packaging comprises a carrier which defines a horizontal upper face. The carrier may, in particular, be a thermoformed film part as is frequently used in the prior art as a component of so-called blister packagings. In order to close the packaging, the packaging may also have a closure layer or a different type of mating part relative to the carrier, which is sealed onto the horizontal upper face, for example a closure layer made of plastics, paper or a composite material. An upwardly open receiver recess is formed in the carrier for receiving the discharge device in a planar manner.

In order to simplify the handling of the discharge device and to design it in a particularly intuitive manner, preferably a closure holding recess is configured in the carrier, said closure holding recess being dimensioned in a complementary manner to the closure. The closure is thus oriented such that it may be inserted into the closure holding recess such that the distal closure end faces upwardly. The closure is able to be received in this orientation, in particular, by a frictional connection in the closure holding recess. In this case the closure holding recess may be configured and dimensioned such that it exerts a lateral clamping force onto the closure if said closure is inserted into the closure holding recess in the corresponding orientation. The closure may, in particular, be receivable in an anti-tilt manner in the closure holding recess. The closure holding recess may be configured separately from the receiver recess or it may be configured as a region of the receiver recess and, for example, may be formed by a partial widening of the receiver recess. In order to permit a particularly intuitive handling, a marking may be applied to the carrier adjacent to the closure holding recess, said marking indicating by graphical elements or text that the corresponding recess is provided for receiving the closure.

An upwardly open separate fluid reservoir recess is also configured in the carrier, said recess permitting a liquid, for example saline solution or blood, to be received. In this manner, the liquid may be readily suctioned by means of the discharge device after the closure has been removed from the discharge device, in order to wet a granulate in the discharge device with the liquid. A separate tray for the liquid is not required. The fluid reservoir recess is preferably configured separately from the receiver recess and the closure holding recess. Also in this case the handling may be designed to be particularly intuitive by a marking being applied to the carrier adjacent to the fluid reservoir recess, said marking indicating by graphical elements or text that the corresponding recess is provided for receiving a liquid.

The discharge device may comprise in a manner known per se a feed element in order to discharge from the container the product received in the container through the discharge opening by advancing the feed element, after removing the separator element. In order to permit in a simple manner the suctioning of liquid by the feed element into the container, the feed element may have a thumb ring.

Depending on the type and quantity of the filling it may be desired to fix the feed element relative to the container in different feed positions in the packaging. Thus, for example, it may be desired to fix the feed element in an intermediate position approximately half-way between an initial position in which the feed element is pulled out to a maximum extent in the proximal direction and an end position in which the feed element has been pushed in to a maximum extent in the distal direction. This is the case, for example, if the container has been prefilled with a granulate which has to be hydrated with a liquid before being administered. On the other hand, it may be desired alternatively to fix the feed element in the initial position. This is the case, for example, if the container is filled with a ready-to-use product. In order to be prepared for both requirements the receiver recess may have a first recess region for receiving the thumb ring, wherein the thumb ring comes to rest in the first recess region when the feed element is located in a first feed position relative to the container, and the receiver recess may have a second recess region for receiving the thumb ring, wherein the thumb ring comes to rest in the second recess region when the feed element is in a second feed position which differs from the first feed position.

A method for producing and for discharging a product, having a discharge device and packaging of the type mentioned above, comprises:

providing the discharge device in a state in which the container is filled with a granulate, the separator element is attached over the discharge opening of the container and the closure is attached to the separator element in the closing position, removing the closure from the separator element whilst the separator element remains on the container;

inserting the closure into the closure holding recess such that the distal closure end faces upwardly;

providing a liquid in the fluid reservoir recess;

receiving the liquid through the separator element into the container in order to wet the granulate with the liquid and thus to produce a product which is ready for discharge;

receiving the closure from the closure holding recess by means of the discharge device so that the closure is connected to the separator element in a reverse orientation relative to the closing position;

unscrewing the separator element from the container by means of the closure; and discharging the product which is ready for discharge through the discharge opening of the container.

In this manner not only is the user prevented from ever having to touch the separator element but also the probability of inadvertent contact is significantly reduced since the user does not need to hold the closure manually in order to connect it to the separator element after receiving the liquid.

In some applications it may be desired to receive the liquid not from an open reservoir such as a tray or a recess in a carrier but to provide the liquid in a closed reservoir such as a syringe. Therefore, a separator element which simplifies the receiving of the liquid from a closed reservoir such as a syringe is proposed.

The separator element forms a proximal end and a distal end and defines an axial direction which extends from the proximal to the distal end. It comprises:

a filter region which is configured to prevent the passage of a granulate in the axial direction between the proximal end and the distal end but to permit the passage of liquid in the axial direction;

and an internal thread which is open toward the proximal end and which extends around the axial direction; and a connecting region which is located distally from the filter region and which forms a female Luer taper which is open toward the distal end.

Many closed reservoirs, in particular commercially available syringes, have an outlet region which forms a male Luer taper. By the proposed design of the separator element, a connection between a reservoir with the male Luer taper and the separator element is simplified by the male Luer taper of the reservoir being able to be inserted in the female Luer taper of the separator element.

An internal taper with a gradient of 6% to the axial direction is denoted as a female Luer taper. Luer connections are standardized in the ISO standard 594-1:2003-08-30 ("Conical fittings with a 6% (Luer) taper for syringes, needles and certain other medial equipment; Part 1: General requirements"). This standard is fully incorporated in the present disclosure by reference. If in the present document reference is made to a Luer connection or a Luer taper, a corresponding structure according to the cited standard is always understood.

The separator element may also have in its connecting region on the outer face at least one engagement element which is configured for an engagement with an internal thread of an attachment. The engagement element may, in particular, be a bayonet flange or a short threaded segment. The engagement element may, in particular, be designed according to the ISO Standard 594-2:2003-08-30 ("Conical fittings with 6% (Luer) taper for syringes, needles and certain other medical equipment; Part 2: Lock fittings"). This standard is also fully incorporated in the present disclosure by reference.

A discharge device which has a separator element of the type mentioned above is also proposed. The discharge device also has a container for receiving a product with a peripheral container wall, a proximal container end, a distal container end and a discharge opening at the distal container end. An external thread is configured on the container wall in the region of the distal container end, said external thread extending around the axial direction. The external thread of the container may be brought into engagement with the internal thread of the separator element in order to attach the separator element to the distal container end.

The discharge device may also be complemented by a closure. The closure has a top wall, an outer wall, a plug which forms a male Luer taper extending from the top wall in a proximal direction, as well as an internal thread which is configured on the outer wall and open toward the proximal end, wherein the internal thread, in particular, is arranged proximally from the top wall. The internal thread is able to be brought into engagement with the aforementioned engagement element which is configured on the outer face on the connecting region of the separator element.

A method for producing and for discharging a product, having a discharge device of the type mentioned above, comprises:

providing the discharge device in a state in which the container is filled with a granulate, the separator element is attached over the discharge opening of the container, and the closure is attached to the separator element in a closing position, removing the closure from the separator element whilst the separator element remains on the container;

connecting a fluid reservoir to the separator element, wherein the fluid reservoir contains a liquid and comprises an outlet region which forms a male Luer taper and wherein the outlet region is inserted into the connecting region of the separator element in order to connect the fluid reservoir to the separator element;

receiving liquid from the fluid reservoir through the separator element into the container in order to wet the granulate with the liquid and thus to produce a product which is ready for discharge;

removing the fluid reservoir and the separator element from the container; and discharging the product which is ready for discharge through the discharge opening of the container.

BRIEF DESCRIPTION OF THE DRAWINGS

Preferred embodiments of the invention are described hereinafter with reference to the drawings which serve merely for explanation and are not to be interpreted as limiting. In the drawings:

FIG. 21 shows a central longitudinal section through the closure of the discharge device of the third embodiment;

FIG. 22 shows a central longitudinal section through the distal end region of the discharge device of the third embodiment, wherein the closure is located in a closing position;

FIG. 23 shows a central longitudinal section through the distal end region of the discharge device of the third embodiment, wherein the closure has been unscrewed and repositioned in reverse orientation;

FIG. 24 shows a sectional view in the plane D-D of FIG. 23;

DESCRIPTION OF PREFERRED EMBODIMENTS

Figure 1:
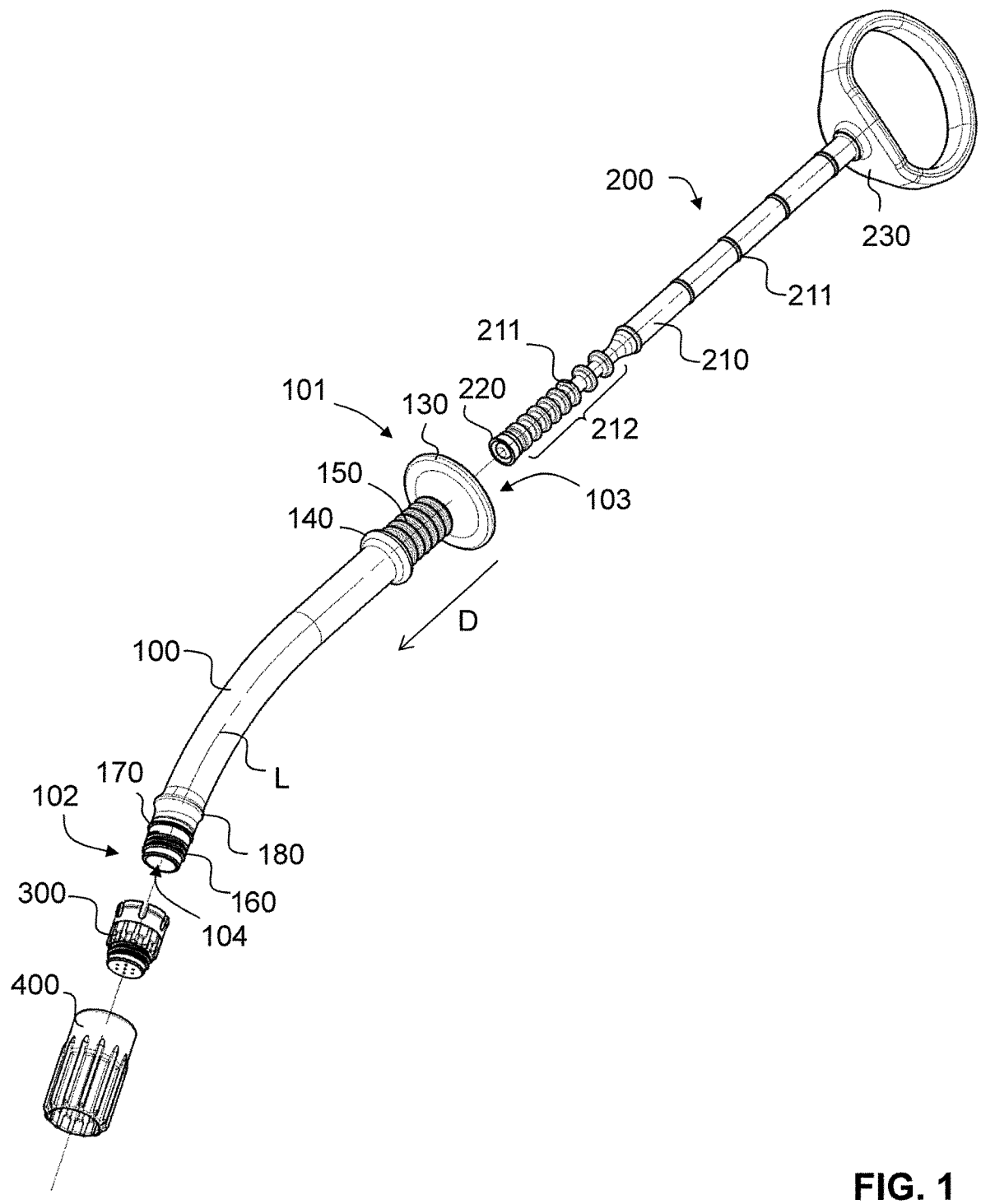
FIG. 1 shows an exploded view of a discharge device according to a first embodiment, with the container, separator element and closure.

In FIGS. 1 to 12 a first exemplary embodiment of a discharge device is illustrated in various views. The discharge device comprises a container 100, a feed element 200, in order to discharge a product received in the container in a distal direction D, a separator element 300 and a closure 400.

The distal direction D is defined as that direction in which the feed element 2 moves into the container 100 in order to discharge the product out of the container 100. The opposing direction is denoted as the proximal direction.

The container 100 which may be identified particularly clearly in FIGS. 1-5 comprises a peripheral container wall 110 which defines a container interior 120, an open proximal container end 101 and an open distal container end 102. The container interior is at least approximately of circular cylindrical shape, wherein the cylinder axis defines a central longitudinal axis L. The clear cross section of the container 100 is at least approximately uniform along the entire distance from the proximal container end 101 to the distal container end 102, wherein optionally the proximal container end may be slightly widened in order to facilitate the insertion of the feed element 200 and wherein in this region an anti-retraction device may be configured in order to prevent the feed element 200 from being fully pulled out of the container 100. The feed element 200 may be inserted at the proximal container end 101 through an insertion opening 103 into the container 100. The central longitudinal axis L of the container 100 extends from the proximal end 101 to the distal end 102 initially in a linear manner but then increasingly curves in a curved region 105 so that the proximal end region and the distal end region of the container extend relative to one another at an angle of curvature α of approximately 30°.

The distal container end 102 forms a discharge opening 104 through which the product may be discharged from the container 100. In the region of the distal container end 102 an external thread 160 is configured on the outer face of the container wall 110, said external thread permitting a connection of the container 100 to the separator element 300 or to the closure 400. Proximally from the external thread an axial locking structure 170 in the form of an annular bead is configured integrally on the outer face of the container wall 110, the function thereof being described hereinafter in more detail. Proximally spaced apart from the axial locking structure 170, a bridging structure 180 in the form of a further annular bead protruding further radially outwardly is configured integrally on the outer face of the container wall 110, the function thereof also being described hereinafter in more detail.

A first finger support 130 in the form of a peripheral flange is configured at the proximal container end 101. Alternatively, for example, two restraining flanks may also be provided. In order to prevent the fingers of the user from slipping if the user grips the container between the index finger and the middle finger and with the thumb wishes to pull the feed element 200 in the proximal direction out of the container, a second finger support 140 is configured on the container wall 110 on the outer face. The second finger support 140 is arranged distally from the first finger support at a spacing therefrom, wherein this spacing approximately corresponds to the thickness of a finger, typically ca. 1.5-3 cm. In the present example, the second finger support 140 is configured as an annular bead which protrudes radially outwardly out of the container wall by ca. 1-2 mm. Between the first and the second finger support a groove structure 150 is configured in the container wall, said groove structure additionally counteracting slippage of the fingers. The finger supports 130, 140 and the groove structure 150 are configured integrally with the container wall 110.

Figure 2:
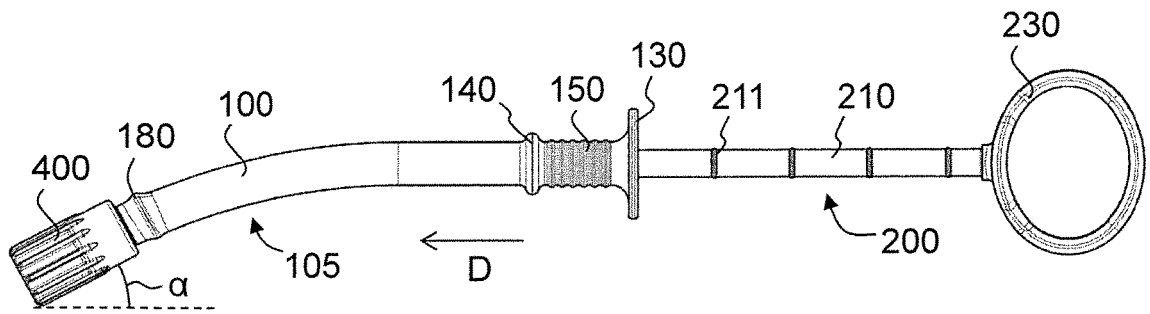
FIG. 2 shows a side view of the discharge device of FIG. 1.
Figure 3:
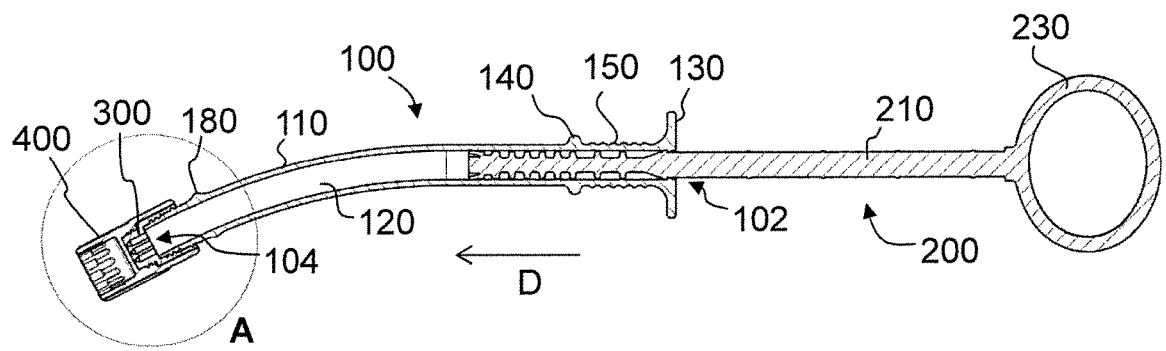
FIG. 3 shows a central longitudinal section through the discharge device of FIG. 1.

The feed element 200 is able to be identified in FIGS. 1-3. The feed element comprises a piston rod 210, a piston 220 being configured at the distal end thereof for feeding a product received in the container 100. The piston 220 in this case bears in a peripherally sealed manner against the inner face of the container wall 110.

In order to reduce the friction between the container wall 110 and the piston rod 210, the piston rod 210 has an external diameter which is smaller than the internal diameter of the container 100. However, in order to ensure correct guidance of the piston rod 210 in the container interior 120, the piston rod 210 has radially outwardly protruding peripheral annular guide beads 211, the external diameter thereof corresponding to the internal diameter of the container 100 so that the guide beads 211 which bear on the inner face against the container wall 110. So that the piston rod 210 may also easily follow the curvature of the container 100, the external diameter of the piston rod 210 is additionally reduced in a distal region 212 and the guide beads 211 are arranged more closely in this region. This lends additional flexibility to the piston rod 210 in the distal region 212 without impairing the lateral guidance of the piston rod 210.

A thumb ring 230 is configured at the proximal end of the piston rod 210, said thumb ring being sufficiently large that the thumb of a user may be inserted. By configuring the thumb support as a ring it is possible not only to insert the feed element 200 by means of the thumb in the distal direction D into the container 100 but also to pull the feed element out of the container in the proximal direction, whilst the container is held between the index finger and the middle finger of the same hand. In this manner, in particular, a liquid may be suctioned into the container.

Figure 6:
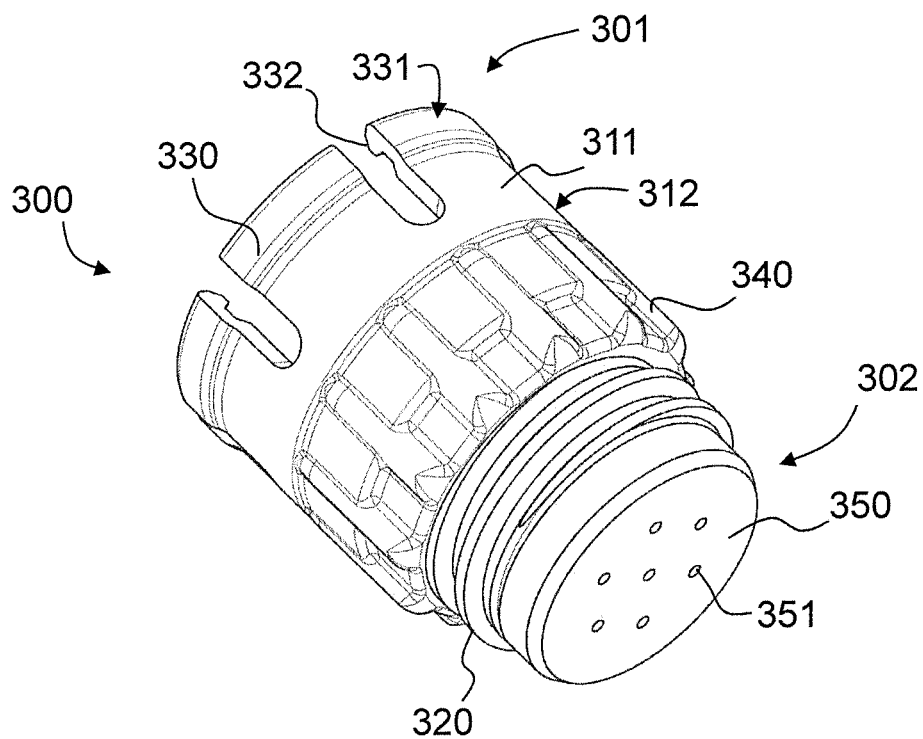
FIG. 6 shows a perspective view of the separator element of the discharge device of FIG. 1.
Figure 7:
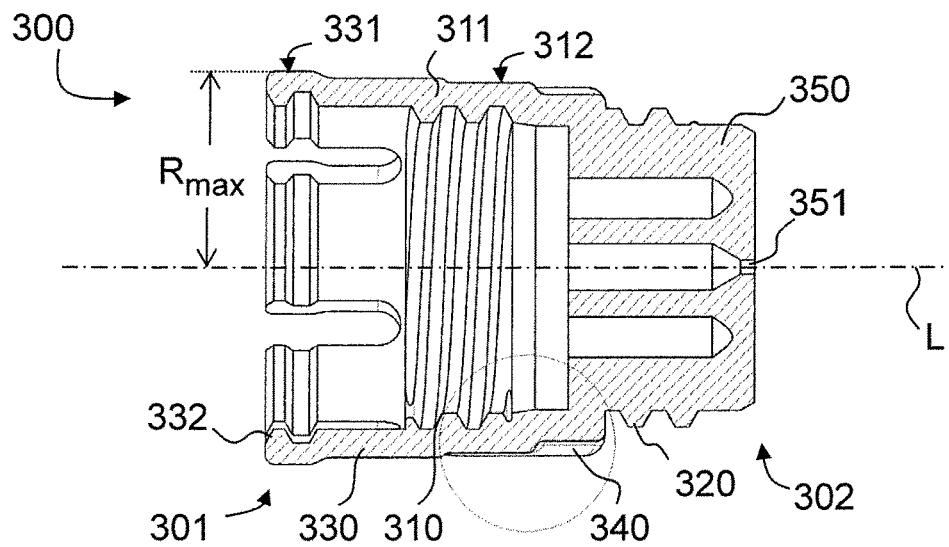
FIG. 7 shows a central longitudinal section through the separator element of FIG. 6.

The separator element 300 is able to be particularly clearly identified in FIGS. 6 and 7. The separator element comprises a filter region 350 which is configured to prevent the passage of a granulate in the distal direction D but to permit the passage of liquid in the proximal direction. To this end, the filter region 350 has a plurality of axial through-openings 351 which extend parallel to the longitudinal axis L. The distal front face of the filter region 350 forms the distal end 302 of the separator element 300.

An external thread 320 is configured on the peripheral outer surface of the filter region 350, said external thread extending around the central longitudinal axis and being open toward the distal end 302, so that from this end the closure 400 may be screwed onto the separator element.

In the proximal direction, a peripheral outer wall region 311 adjoins the filter region 350, on the inner face thereof an internal thread 310 being configured, said internal thread being coaxial with the external thread 320 and open toward the proximal end in order to be able to screw the separator element 300 onto the distal container end 102.

Starting from the outer wall region 311 a plurality of similar resilient locking arms 330 extend in the proximal direction. The function of the locking arms is described in more detail hereinafter. The free ends of the locking arms 330 form the proximal end 301 of the separator element 300. At their free ends the locking arms 330 in each case have a rear-engagement element 332 extending inwardly in the form of a locking lug. The locking arms 330 have an outer surface 331 on their respective free end. These outer surfaces 331 define the maximum radius $R_{max}$ of the separator element. These outer surfaces are arranged further radially outwardly than the outer surface 312 of the outer wall region 311 distally adjoining the locking arms.

Figure 8:
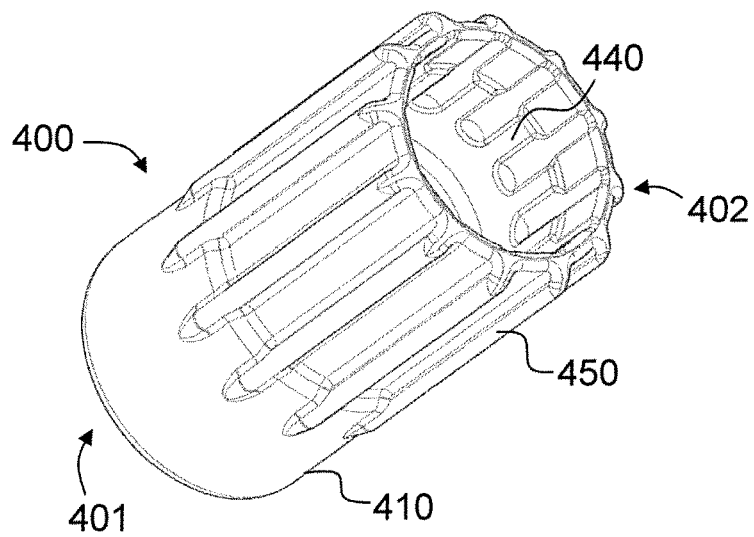
FIG. 8 shows a perspective view of the closure of the discharge device according to FIG. 1.
Figure 9:
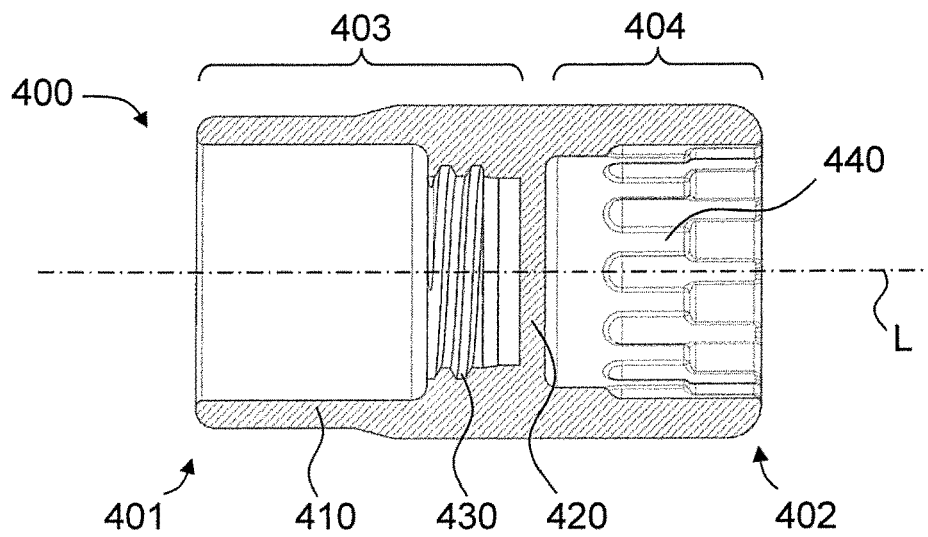
FIG. 9 shows a central longitudinal section through the closure of FIG. 8.

The closure 400 is able to be particularly clearly identified in FIGS. 8 and 9. The closure has a proximal end 401, a distal end 402, a peripheral outer wall 410 and a top wall 420. The closure is of tubular basic shape, wherein it is subdivided by the top wall 420 into a proximal portion 403 and a distal portion 404. Both the proximal portion 403 and the distal portion 404 are hollow and the closure is open both at the proximal end 401 and at the distal end 402. In the proximal portion 403 an internal thread 430 is configured on the inner face in the outer wall 410. The outer wall 410 extends proximally significantly beyond the internal thread 430. In the distal portion 404 a plurality of drivers 440 in the form of axially extending ribs are configured on the inner face in the outer wall 410. On the outer face, the closure has a plurality of longitudinal ribs 450 in order to prevent a user from slipping when handling the closure.

During production, the container 100 is filled with a granulate (not shown). As is revealed, in particular, from FIG. 4, the separator element 300 is attached to the distal container end 102 via the distal discharge opening 104, wherein the internal thread 310 of the separator element comes into engagement with the external thread 160 of the container. The closure 400 is mounted on the separator element 300, wherein the internal thread 430 of the closure is in engagement with the external thread 320 of the separator element 300. In this case, the top wall 420 of the closure axially bears against the distal front face of the filter region 350 with the through-openings 351. The outer wall 410 of the closure entirely covers the filter element 300 radially, so that in this state the user is not able to touch the filter element 300. The outer wall 410 extends, in particular, beyond the locking arms 330. In this case, the outer wall bears against the outer surfaces 331 of the locking arms 330 and as a result forces the locking arms 330 radially inwardly. As a result, the rear-engagement elements 332 (in this case locking lugs) come into axial positive engagement with the axial securing element 170 (in this case an annular bead) so that the separator element 300 may no longer be removed in the distal direction from the container 100.

Figure 4:
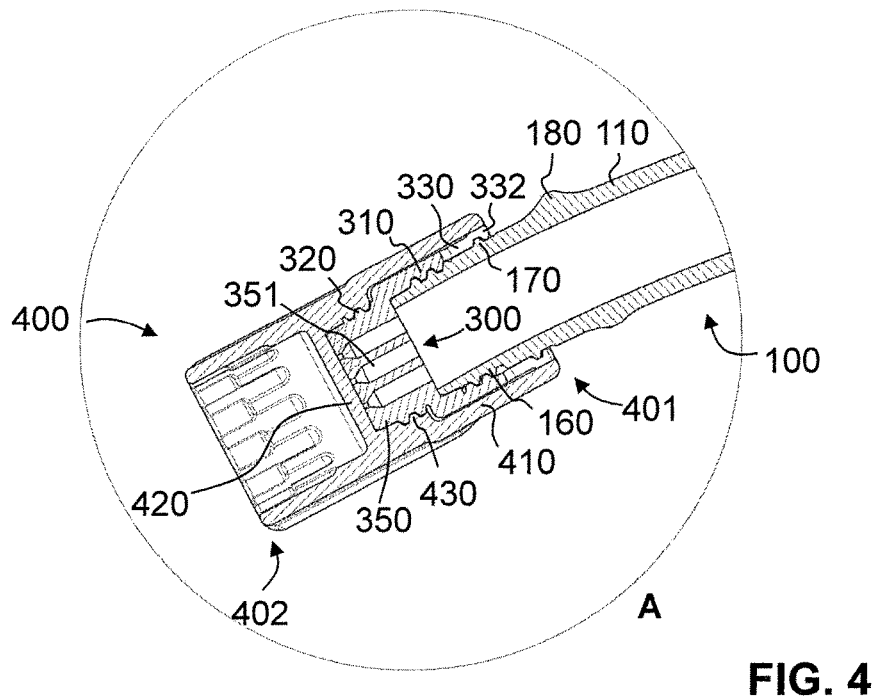
FIG. 4 shows a detailed view of the region A of FIG. 3.
Figure 5:
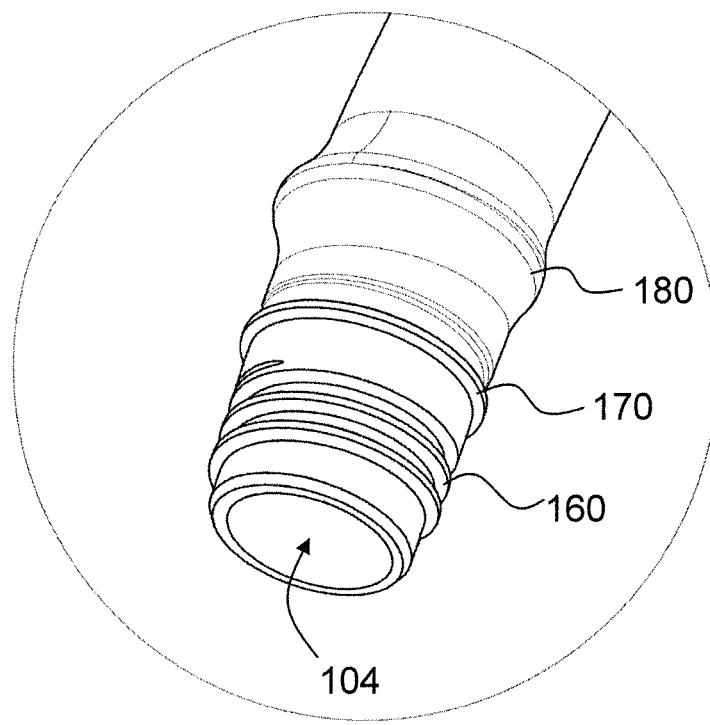
FIG. 5 shows a detailed view of the distal end of the container of the discharge device of FIG. 1.

This results in the state of FIGS. 2-4. In this form the discharge device is delivered.

For using the discharge device, the user now unscrews the closure 400. The engagement of the rear-engagement elements 332 with the axial securing element 170 also prevents the separator element 300 from being entrained at the same time. The separator element 300 thus remains on the distal discharge opening of the container 100 and prevents the granulate from escaping from the container 100. To this end, the through-openings 351 have a diameter which is smaller than the average grain size of the granulate, determined by a sieve analysis according to DIN EN 933-1:2012-03.

Now a liquid, for example blood or physiological saline solution, is introduced through the separator element 300 into the container 100. To this end, different options are available. Thus the liquid, for example, may be injected by a syringe cannula through the through-openings or the liquid may be suctioned into the container by the feed element 200 being pulled back.

Figure 10:
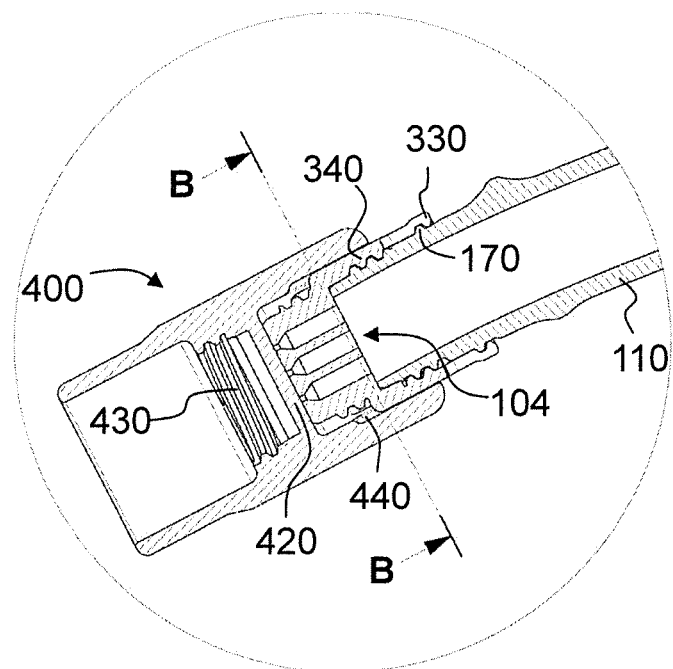
FIG. 10 shows a central longitudinal section through the distal end region of the discharge device of FIG. 1, wherein the closure is positioned in the reverse orientation.
Figure 11:
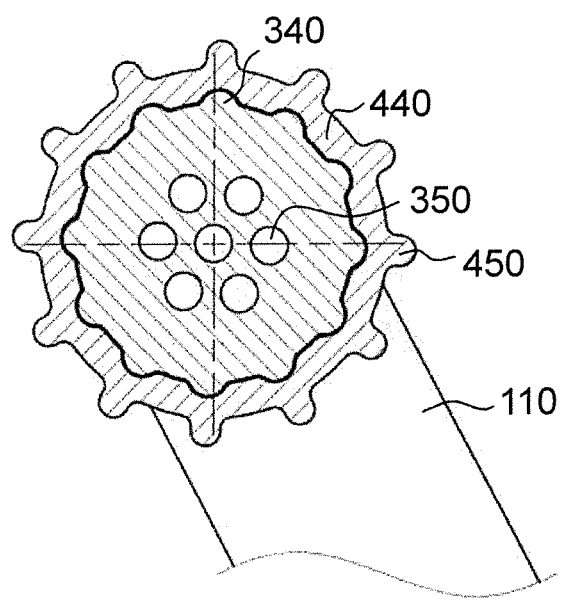
FIG. 11 shows a sectional view in the plane B-B of FIG. 10.

In order to discharge the product thus produced, the separator element 300 is removed from the container 100. To this end, the closure 400 is rotated by 180 degrees around the transverse direction and pushed in reverse orientation onto the separator element 300. This state is illustrated in FIGS. 10 and 11. In this case, the drivers 440 come into engagement on the inner face of the outer wall 410 of the closure with the driver elements 340 on the outer face of the separator element 300 so that a positive connection is produced between the separator element 300 and the closure 400 in the peripheral direction. As a result, the separator element 300 may now be unscrewed from the container 100 by means of the closure 400 without the user having to touch the separator element 300. The axial engagement between the rear-engagement elements 332 and the axial locking structure 170 is now released, since the locking arms 330 may now spring outwardly.

Figure 12:
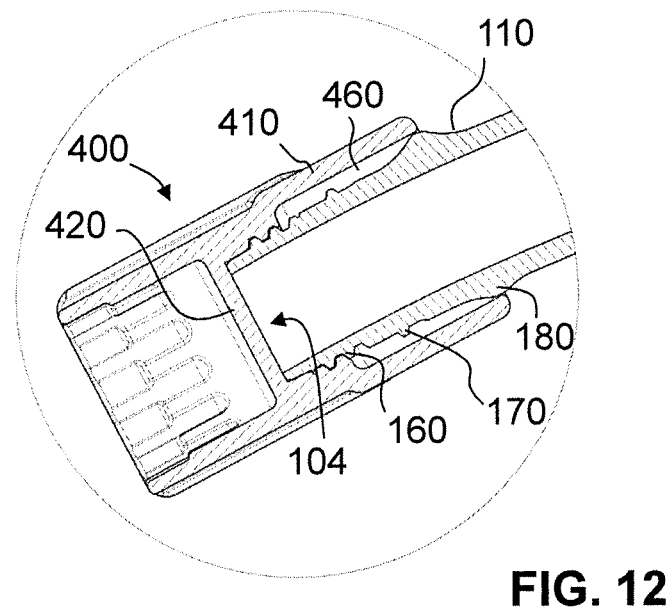
FIG. 12 shows a central longitudinal section through the distal end region of the discharge device of FIG. 1, wherein the separator element has been omitted and the closure has been screwed directly onto the container.

If the container has been already prefilled with a ready-to-use product, the separator element 300 may be dispensed with and the closure 400 may be directly attached over the discharge opening of the container 100. However, the same container 100 and the same closure 400 may be used, i.e. no structural alterations are required. This situation is illustrated in FIG. 12. The outer wall 410 of the closure 400 now extends in this case at a radial distance from the outer face of the container wall 110 so that an annular radial intermediate space 460 is formed between the container wall 110 and the outer wall 410 of the closure 400. In this case, the outer wall 410 of the closure, in particular, also radially covers the axial locking structure 170. In order to prevent debris from penetrating the intermediate space 460, the aforementioned bridging structure 180 is provided on the outer face of the container wall 110. This extends sufficiently far radially outwardly in order to bridge the intermediate space 460 and to close this space in the proximal direction. In this case, the proximal end of the outer wall 410 is located on the radial outer face of the bridging structure 180. Optionally, a seal may be configured here.

A second exemplary embodiment is illustrated in FIGS. 13-16. The same or similar-acting elements are denoted by the same reference numerals as in the first exemplary embodiment. The second exemplary embodiment differs from the first exemplary embodiment only by the design of the distal end region of the container 100 and the locking elements 330 on the separator element 300.

Figure 13:
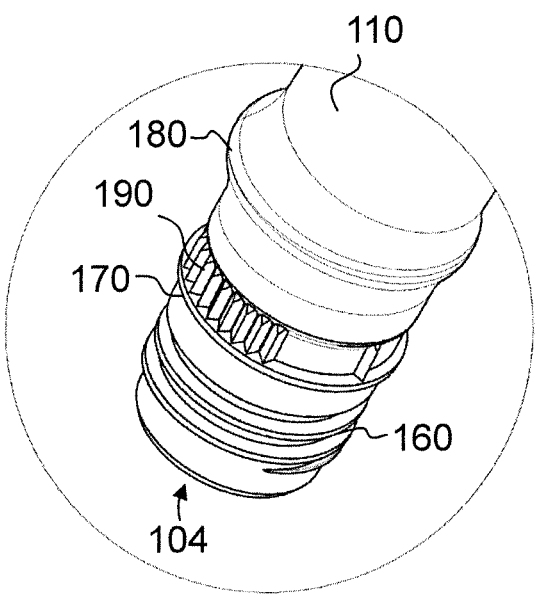
FIG. 13 shows a perspective view of the distal end of the container of a discharge device according to a second embodiment.

The distal end region of the container 100 is illustrated in FIG. 13. A rotational locking structure 190 in the form of an external toothing is configured between the axial locking structure 170 (in this case an annular bead) and the bridging structure 180 (in this case also an annular bead) on the container wall 110 on the outer face. In order to permit improved unmolding during injection-molding, this external toothing is not configured continuously over the outer periphery but interrupted in some regions.

Figure 14:
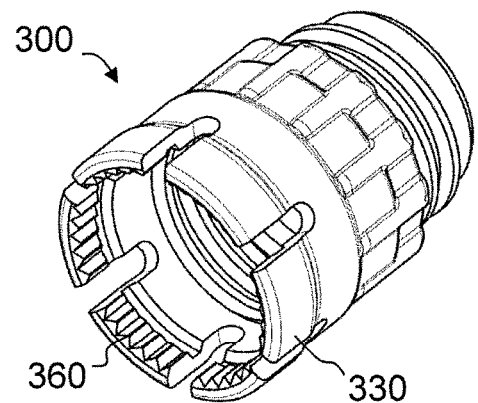
FIG. 14 shows a perspective view of the separator element of the discharge device of the second embodiment.

As is revealed from FIG. 14, at the proximal end of each locking arm 330 an internal toothing 360 which is complementary thereto is configured. This also forms here at the same time the rear-engagement elements for an axial securing on the axial locking structure 170.

Figure 15:
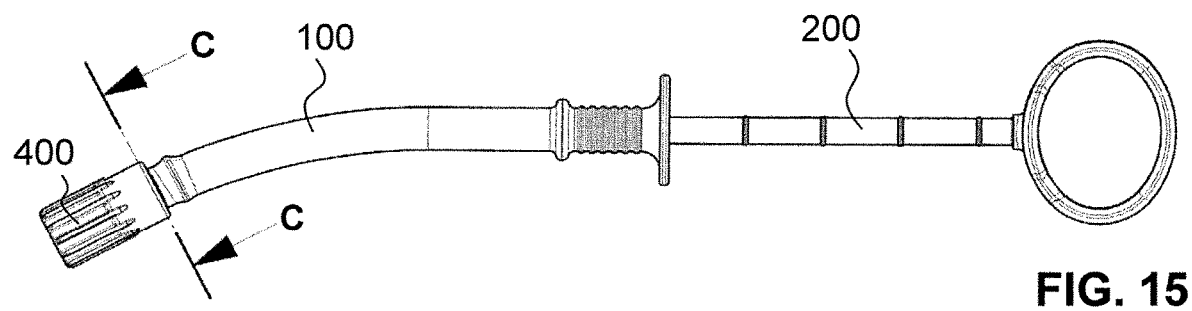
FIG. 15 shows a side view of the discharge device according to the second embodiment.
Figure 16:
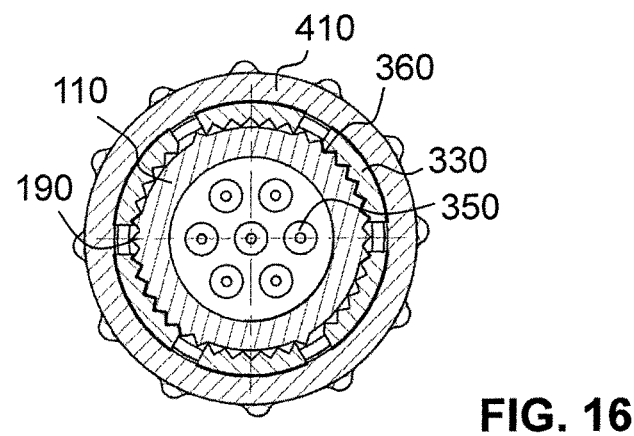
FIG. 16 shows a sectional view in the plane C-C of FIG. 15.
Figure 17:
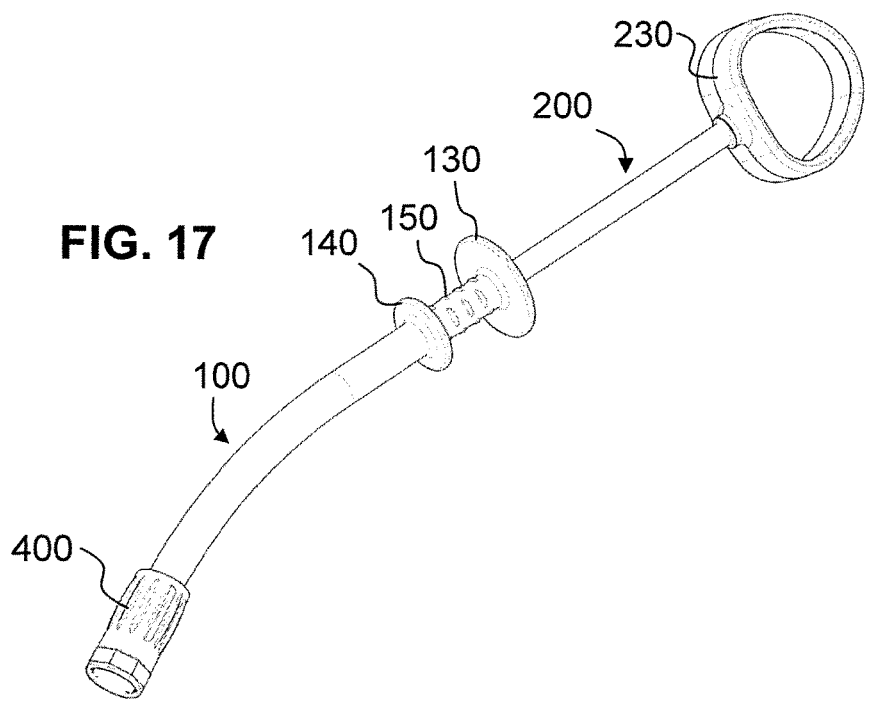
FIG. 17 shows a perspective view of a discharge device according to a third embodiment.
Figure 18:
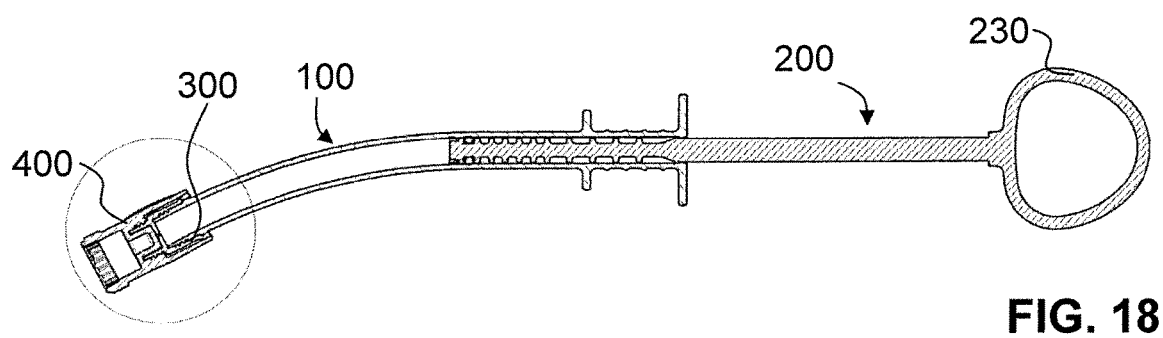
FIG. 18 shows a central longitudinal section through the discharge device of the third embodiment.

As is illustrated in FIGS. 15 and 16, in this manner the separator element 300 is secured not only in the axial direction but also relative to rotations on the container 100 when the closure 400 is screwed onto the separator element 300. In this case, the outer wall 410 of the closure presses the locking arms 330 again inwardly so that the internal toothing 360 comes into positive engagement both with the rotational locking structure 190 relative to the peripheral direction and with the axial locking structure 170 relative to the distal direction. Thus when unscrewing the closure it is additionally ensured that the separator element 300 remains on the container.

A third exemplary embodiment is illustrated in FIGS. 17 to 24. The same or similar-acting elements are again denoted by the same reference numerals as in the previous exemplary embodiments.

The third exemplary embodiment differs from the second exemplary embodiment primarily by the design of the separator element 300 and the closure 400. In addition, small differences are present in the design of the first and second finger supports 130, 140 and the groove structure 150 arranged therebetween and in the shaping of the thumb ring 230.

Figure 19:
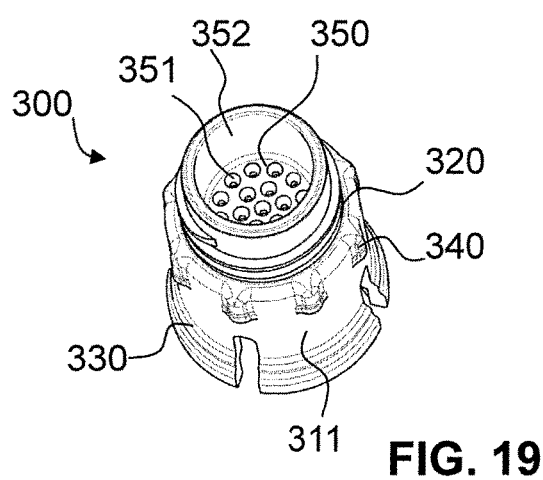
FIG. 19 shows a perspective view of the separator element of the discharge device of the third embodiment.
Figure 20:
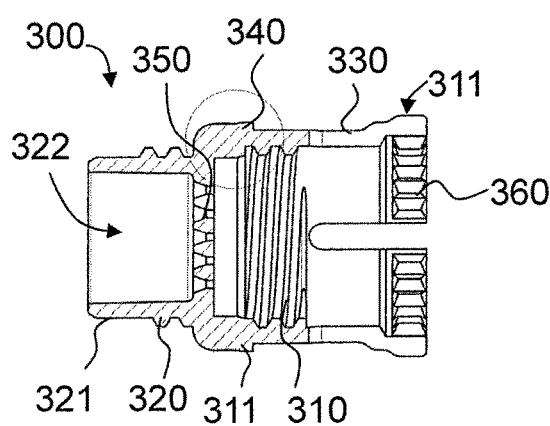
FIG. 20 shows a central longitudinal section through the separator element of FIG. 19.
Figure 25:
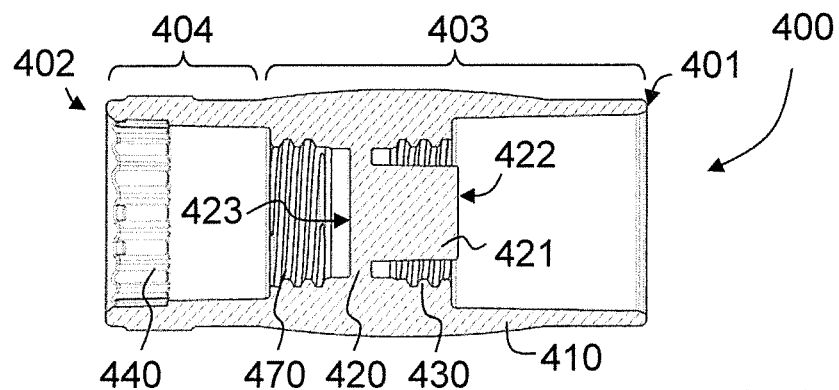
FIG. 25 shows a central longitudinal section through the closure of a discharge device according to a fourth embodiment.

The separator element 300 of the third exemplary embodiment is shown alone in FIGS. 19 and 20. In contrast to the first and second exemplary embodiment, the filter region 350 does not extend to the distal end of the separator element 300 but the filter region 350 is configured as a relatively thin plate with a plurality of openings 351. A pipe connector 321 which forms the distal end of the separator element 300 adjoins the filter region 350 in the distal direction. The pipe connector 321 is hollow and thus defines a cavity 322 which is defined in the peripheral direction by the pipe connector 321 and in the proximal direction by the filter region 350. The external thread 320 is configured in this exemplary embodiment on the outer face of the pipe connector 321. By this design, the production of the separator element is simplified in an injection-molding method. In the region of the external thread the unmolding may be carried out in a simple manner using a rotatable core, whilst in the first two exemplary embodiments complicated measures are required for the unmolding.

In contrast to the first two exemplary embodiments, the driver elements 340 of the separator element of the third exemplary embodiment radially protrude slightly beyond the adjoining outer wall region in the proximal direction.

In the region of the proximal end, the design of the separator element otherwise substantially corresponds to that of the second exemplary embodiment. In this regard, reference is made to the above description.

In FIG. 21 the closure of the third exemplary embodiment is shown alone. As in the first and second exemplary embodiment the closure is subdivided into a proximal portion 403 and a distal portion 404. In contrast to the first and second exemplary embodiment a plug 421 is configured on the top wall 420, which is connected to the outer wall 410 on the periphery, said plug being connected to the outer wall 410 at its distal end by an annular top wall region. The plug 421 extends in the interior of the closure 400 in the proximal direction. At its free proximal end the plug 421 forms a distal front face 422. In the present example, the top wall 420 effectively forms the plug 421 by its path. The internal thread 430 is configured in a region of the outer wall 410 which radially surrounds the plug 421.

In the distal portion 404, the closure 400 of the third exemplary embodiment is substantially configured the same as in the first and second exemplary embodiment. In particular, once again adjoining the distal end 402 on the inner face, the outer wall 410 of the closure has drivers 440 which are configured in a complementary manner to the driver elements 340 of the separator element 300. Due to the slightly different shape of the driver elements 340 the shaping of the drivers 440 differs slightly from the shaping in the first and second exemplary embodiment.

In FIGS. 22 to 24 the cooperation of the closure 400 of the third exemplary embodiment with the separator element 300 is illustrated. In FIG. 22 the closure 400 is in the closing position. To this end, the closure is screwed by means of its internal thread 430 onto the external thread 320 of the separator element 300. In this case, the outer wall 410 in the proximal portion once again covers the locking arms 330 of the separator element 300, as has already been described above for the first and second exemplary embodiment. The plug 421 protrudes in the proximal direction into the cavity 352 and namely sufficiently far that the proximal front face 422 bears directly against the distal side of the filter region 350. In this manner, particularly fine particles of a granulate received in the container 100, which may penetrate the filter region 350, are prevented from being able to collect in the cavity 352.

In order to wet the granulate received in the container 100 with a liquid, the closure 400 is unscrewed and liquid is suctioned into the container 100 as has been described in greater detail in connection with the first and second exemplary embodiment. In order to remove the separator element 300 subsequently from the container 100, the closure 400 is again placed onto the separator element 300 in the reverse orientation, and the separator element 300 is unscrewed by means of the closure from the container 100. This situation is illustrated in FIGS. 23 and 24, wherein the cooperation of the driver elements 340 and the drivers 440 may be identified particularly clearly in FIG. 24.

A fourth exemplary embodiment is illustrated in FIGS. 25 to 28. This exemplary embodiment differs from the third exemplary embodiment only by the design of the closure which is shown alone in FIG. 25. In this exemplary embodiment, the closure has a second internal thread 470 between the plug 421 and the distal end 402 of the closure, said second internal thread being dimensioned to be the same as the first internal thread 430 but in contrast to the first internal thread 430 being open toward the distal end 402. The plug 421 in this exemplary embodiment is configured as a solid cylinder so that the top wall 420 on the distal rear face of the plug 421 forms a planar distal front surface 423 which is planar over the entire clear cross section of the plug. The second internal thread 470 adjoins a planar distal front face 423 in the distal direction.

Such a closure is primarily advantageous if optionally a granulate to be wetted or a ready-to-use product is to be received in the same container 100 and the container is intended to be closed by the same closure. This is described in more detail with reference to FIGS. 26 to 28.

Figure 26:
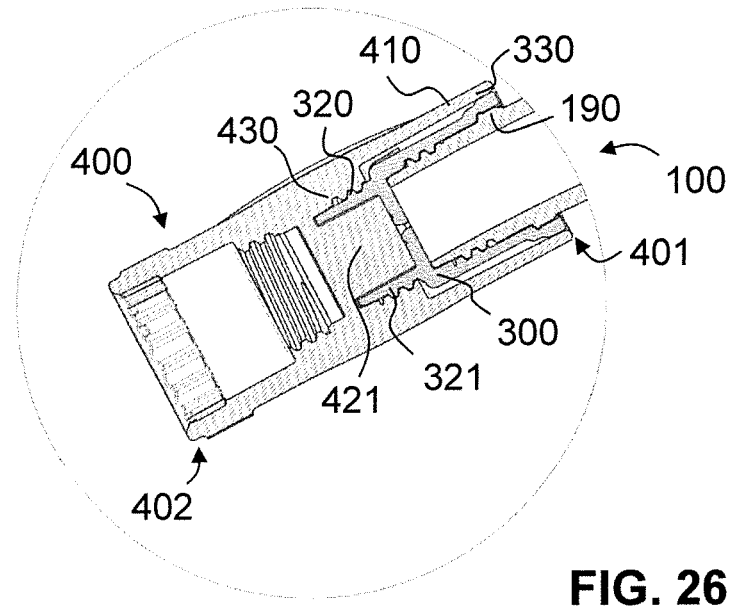
FIG. 26 shows a central longitudinal section through the distal end region of the discharge device of the fourth embodiment, wherein the closure is in a closing position.

In FIG. 26 the situation is shown in which the closure is screwed onto a separator element 300, wherein the separator element 300 is designed to be exactly the same as in the third exemplary embodiment. In particular, the plug 421 protrudes into the cavity which is defined by the pipe connector 321 of the separator element 300.

Figure 27:
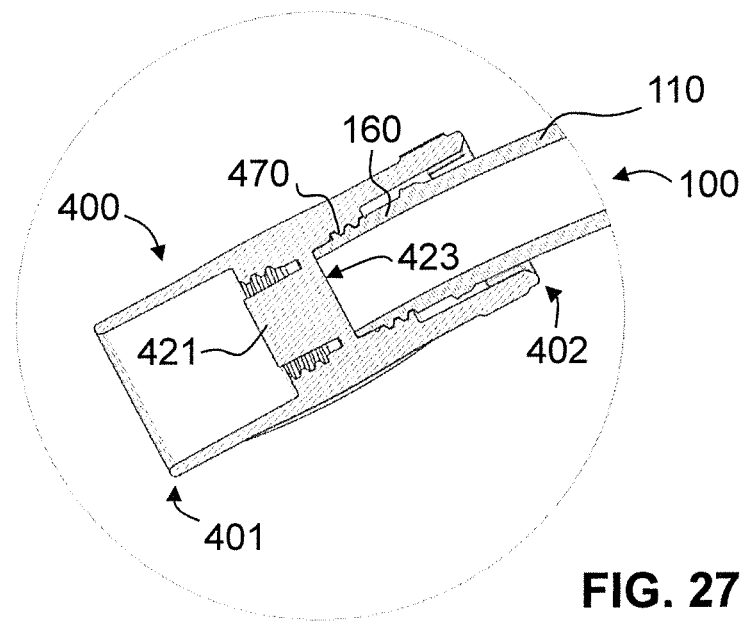
FIG. 27 shows a central longitudinal section through the distal end region of the discharge device of the fourth embodiment, wherein the separator element has been removed and the closure has been screwed onto the free end of the container in reverse orientation.

In FIG. 27, the situation is shown in which the closure 400 is screwed in reverse orientation directly onto the distal end of the container 100. In this case, the second internal thread 470 engages in the external thread 160 on the distal container end. The distal front face 423 on the rear face of the plug 421 bears flat against the distal container end and thereby covers this distal container end. As a result, no element of the closure 400 protrudes into the interior of the container 100. If, in contrast, the closure 400 were to be screwed in the orientation of FIG. 26 onto the distal container end, the plug 421 would protrude into the interior of the container 100 and material which is located in this region would penetrate therein. This is avoided by the proposed design with a second internal thread. In this manner, optionally the same closure may be used in order to be screwed onto a separator element or it may be used in order to be screwed directly onto the container end.

Figure 28:
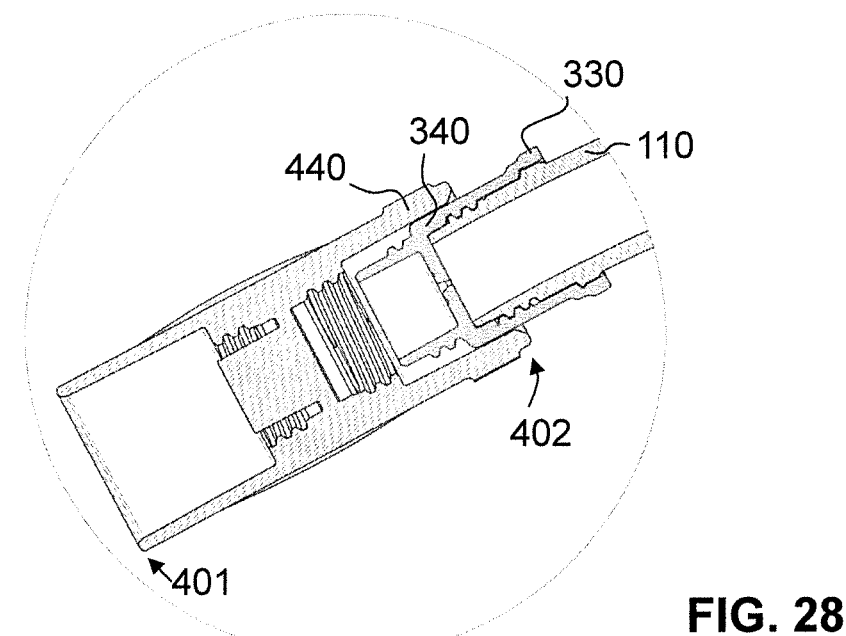
FIG. 28 shows a central longitudinal section through the distal end region of the discharge device of the fourth embodiment, wherein the closure has been pushed onto the separator element in reverse orientation.

For the sake of completeness, in FIG. 28 the situation is illustrated in which the closure has been pushed onto the separator element in the reverse orientation in order to unscrew said separator element from the container. In this regard, the closure of the fourth exemplary embodiment has all of the functionalities of the closure of the other exemplary embodiments.

Figure 29:
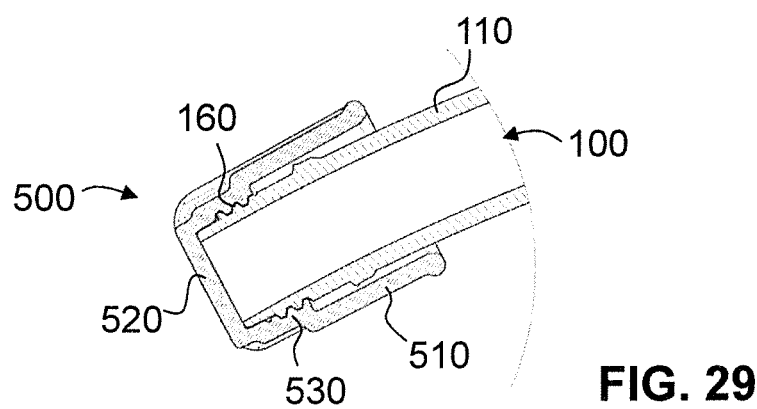
FIG. 29 shows a central longitudinal section through the distal end region of a discharge device according to a fifth embodiment.

A fifth exemplary embodiment is illustrated in FIG. 29. In this exemplary embodiment in the case where the container is to be directly closed, a separate cap closure 500 is provided, said cap closure conventionally having an outer wall 510 with an internal thread 530 and a top wall 520.

In FIGS. 30 to 35 the combination of a discharge device 1 of the above-described type with a packaging 600 is illustrated. The packaging 600 is configured as blister packaging. The packaging has a carrier 610 which in the conventional manner is configured as a thermoformed film part. The carrier 610 defines a horizontal upper face. The carrier 610 has an upwardly open receiver recess 620 for receiving the discharge device 1 in a planar manner. The receiver recess is subdivided into a plurality of portions, namely into a first portion 621, which receives the distal end of the discharge device 1 with the closure 400, a second portion 622 which receives the curved portion of the container 100, a third portion 623 in which the receiver recess is significantly widened for simplified removal of the discharge device 1, a fourth portion 624 for receiving the two finger supports and the region located therebetween and a fifth and sixth portion 625, 626 which in each case are configured for receiving the thumb ring 230.

Figure 30:
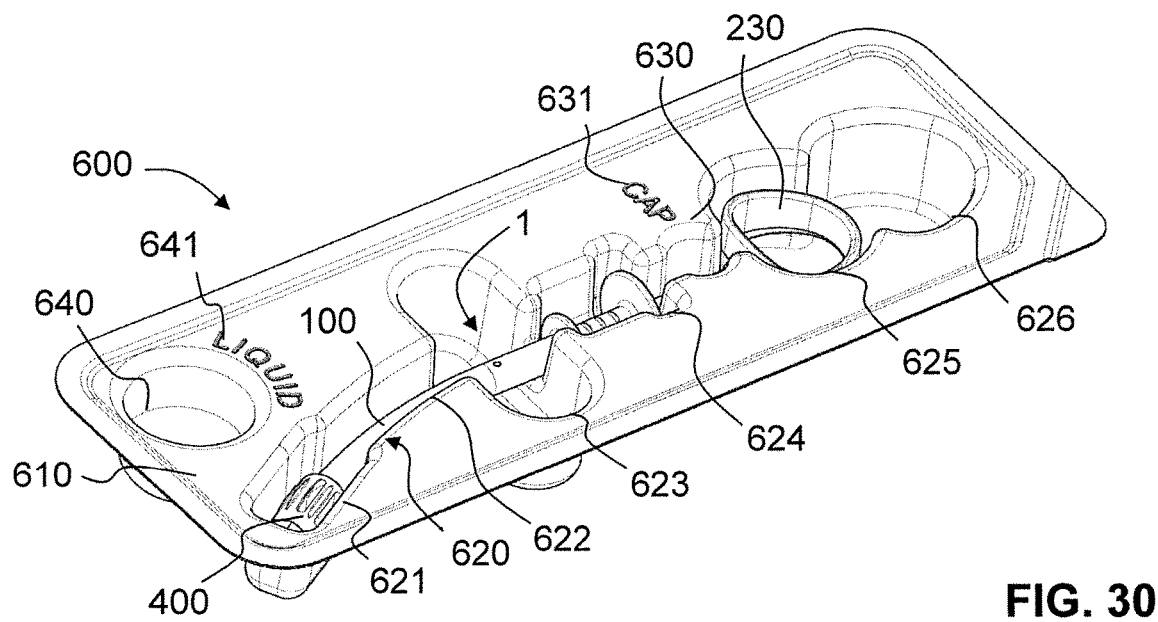
FIG. 30 shows a perspective view of a packaging element with the discharge device received therein.
Figure 31:
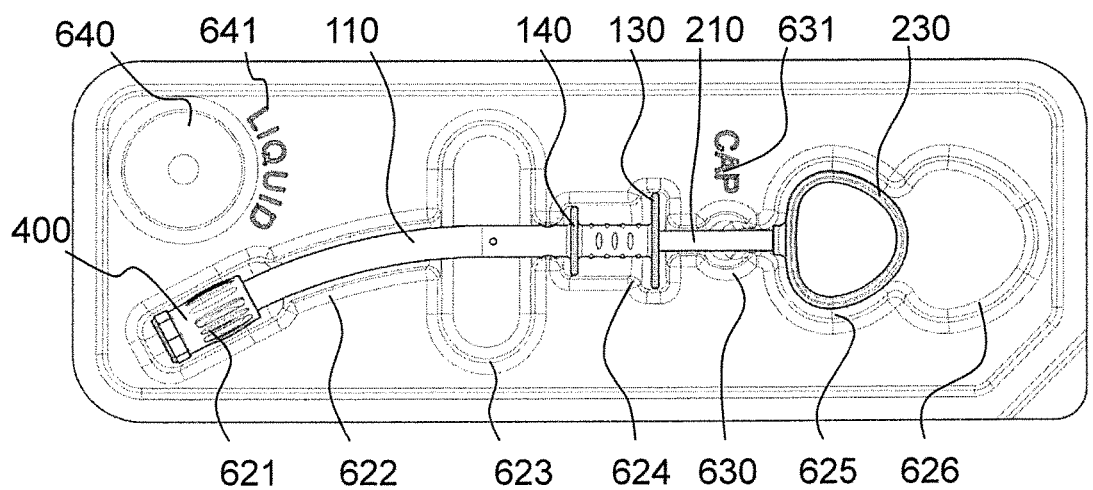
FIG. 31 shows a plan view of the packaging element with the discharge device according to FIG. 30 received therein.

The discharge device 1 is inserted into the receiver recess 620, wherein in the situation of FIGS. 30 and 31 the thumb ring 230 comes to rest in the fifth portion 625 of the receiver recess 620. Here, the container is filled approximately half-way with a granulate to be wetted and closed by a separator element 300 and a closure 400 according to the third exemplary embodiment. Alternatively, a closure 400 according to one of the other exemplary embodiments could also be provided. The feed element 200 is inserted approximately half-way into the container 100. After removing the discharge device 1 and removing the closure 400, therefore, it is possible to suction a liquid into the container 100 through the separator element 300, by the feed element 200 being pulled back by means of the thumb ring 230.

Figure 32:
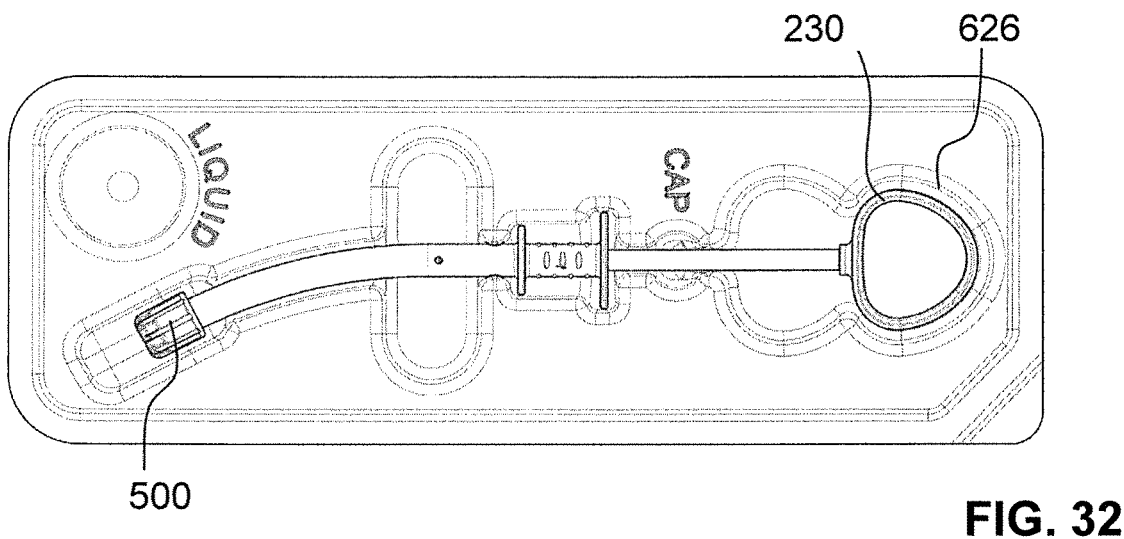
FIG. 32 shows a plan view of the packaging element with the discharge device received therein in a second position with the feed element pulled further out.

In the situation of FIG. 32, however, the container is entirely filled with a product which is ready for discharge (for example a prepared bone graft material) and the feed element 200 is accordingly fully retracted so that the thumb ring 230 comes to rest in the portion 626 of the receiver recess 620. The container in this case is directly closed (without the separator element located therebetween) by the closure 500 of the fifth exemplary embodiment (according to FIG. 29) but could also be closed by the closure 400 of the other exemplary embodiments.

Figure 33:
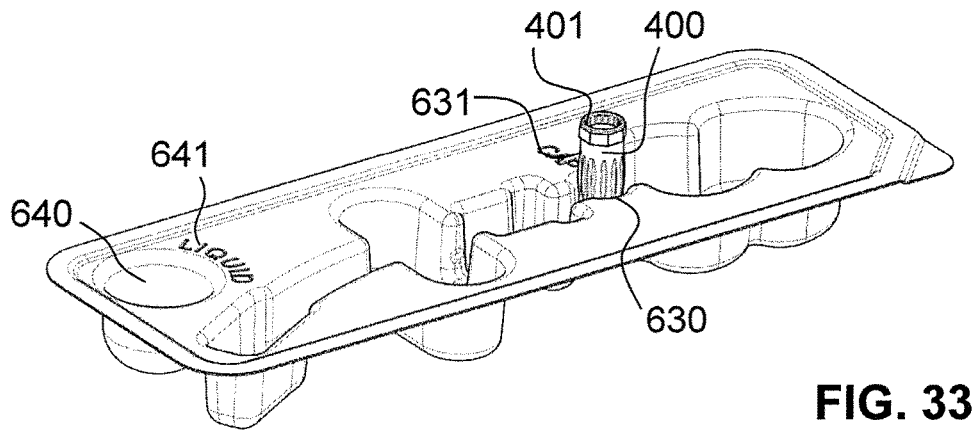
FIG. 33 shows a perspective view of the packaging element with the closure inserted.

Between the portions 624 and 625 is located a further portion of the receiver recess 620 which forms a closure holding recess 630. The closure holding recess 630 is dimensioned so as to be complementary to the closure 400. As a result, the closure 400 may be inserted into the closure holding recess such that the distal closure end faces upwardly. This situation is illustrated in FIG. 33. In addition to the closure holding recess 630, a corresponding marking 631 ("CAP") is configured on the carrier.

Additionally, an upwardly open separate fluid reservoir recess 640 is configured in the carrier 610 in order to receive a liquid such as saline solution or blood. The fluid reservoir recess 640 is marked with a corresponding marking 641 ("LIQUID").

Figure 34:
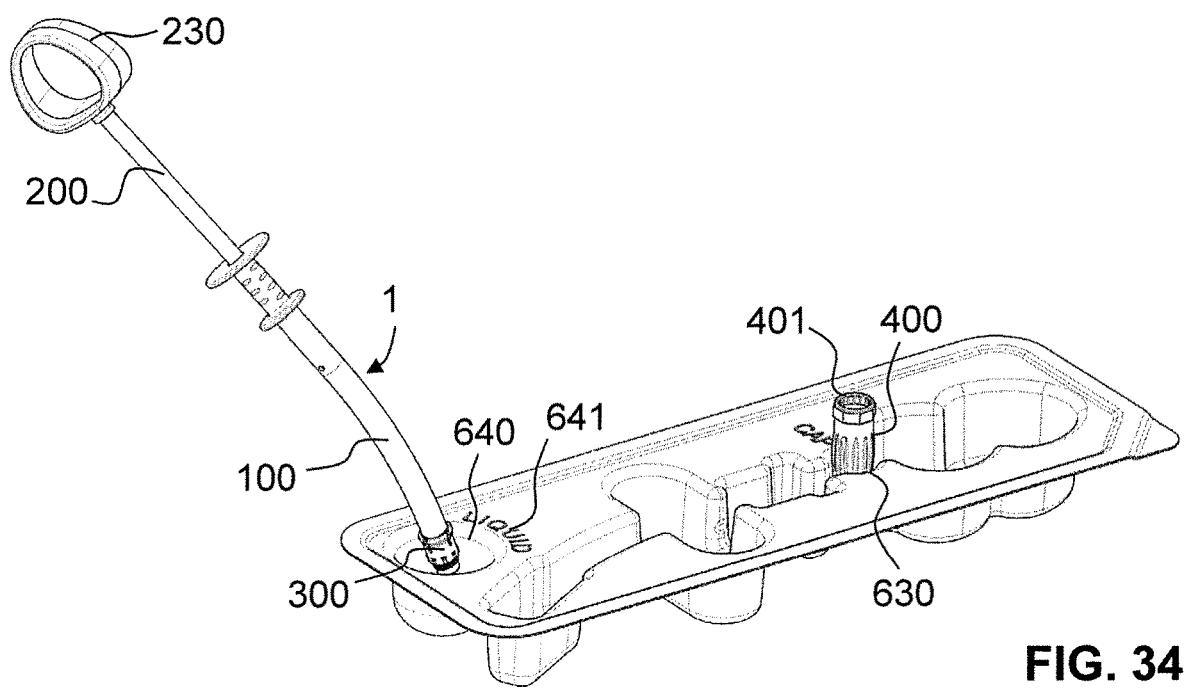
FIG. 34 shows a perspective view of the packaging element and the discharge device for illustrating the use for receiving a liquid in the discharge device.
Figure 35:
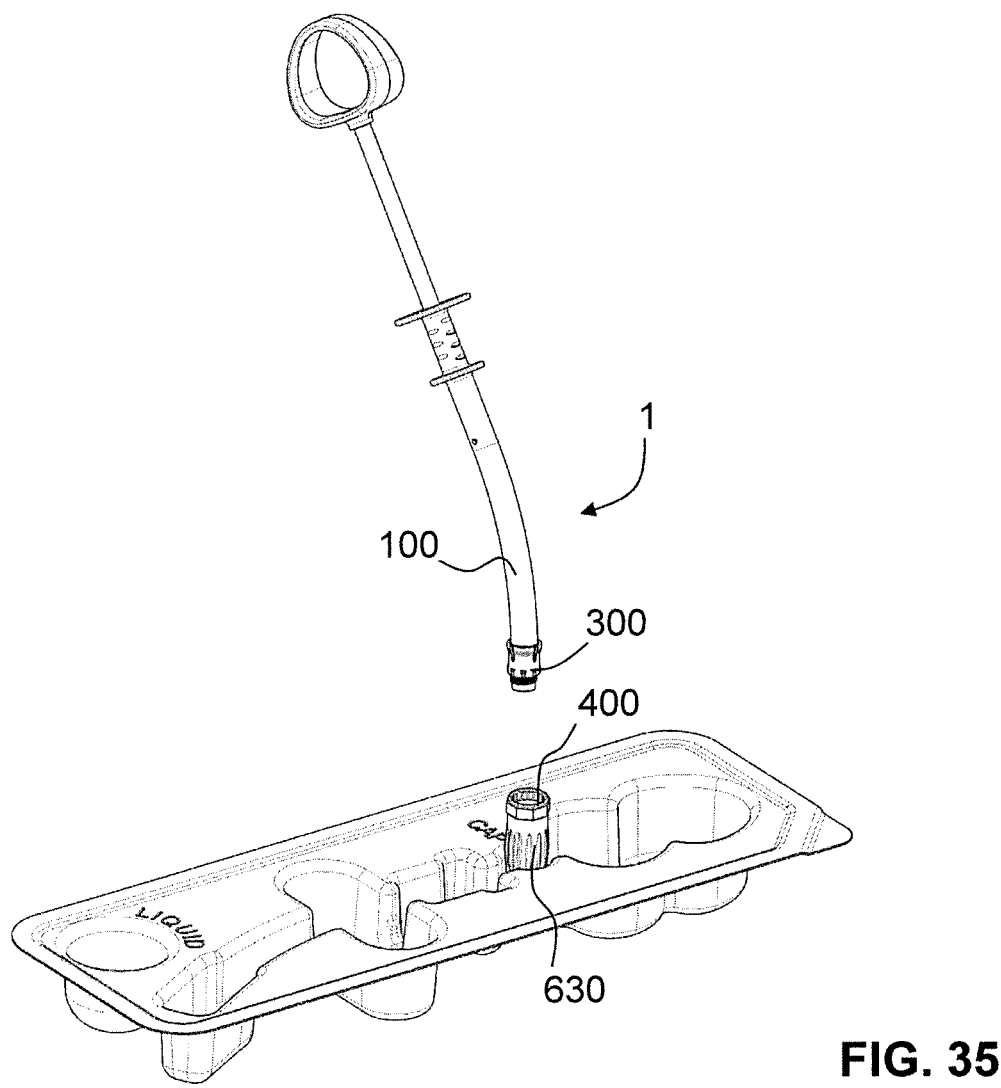
FIG. 35 shows a perspective view of the packaging element and the discharge device for illustrating the connection of the discharge device with the closure after a liquid has been received in the discharge device.

The use of the packaging 600 is illustrated in FIGS. 34 and 35. The user removes the discharge device 1 prefilled with granulate from the carrier 610. To this end, it may be required that initially the user removes a top layer, not shown, from the carrier 610, for example a plastics film which in the delivery state covers the entire upper face of the carrier 610 in order to protect and to keep sterile the contents of the packaging. The user then unscrews the closure 400 from the separator element 300 and inserts the closure with the distal end 401 upwardly into the closure holding recess 630 (see FIG. 34). Now the user dispenses a liquid, for example saline solution or blood, into the fluid reservoir recess 640. The user then grips the discharge device 1, immerses the separator element 300 into the liquid in the fluid reservoir recess 640 and suctions this liquid into the container 100 by pulling back the feed element 200 by means of the thumb ring 230 in the proximal direction P. As a result, the granulate in the container is wetted by the liquid.

After this process, the separator element 300 is externally contaminated by the liquid and should no longer be touched. In order to remove the separator element 300 without touching it, the user inserts the discharge device 1 with the separator element 300 into the closure 400 and in this manner removes the closure 400 from the closure holding recess 630 (see FIG. 35). Now the user may unscrew the separator element 300 by means of the closure 400 from the container 100 without touching the separator element 300. Then the user may discharge the wetted granulate. As a whole, in this manner at no time does the user come into contact with the contaminated separator element 300. Moreover, there is no risk of the user inadvertently coming into contact with the contaminated separator element 300.

Figure 36:
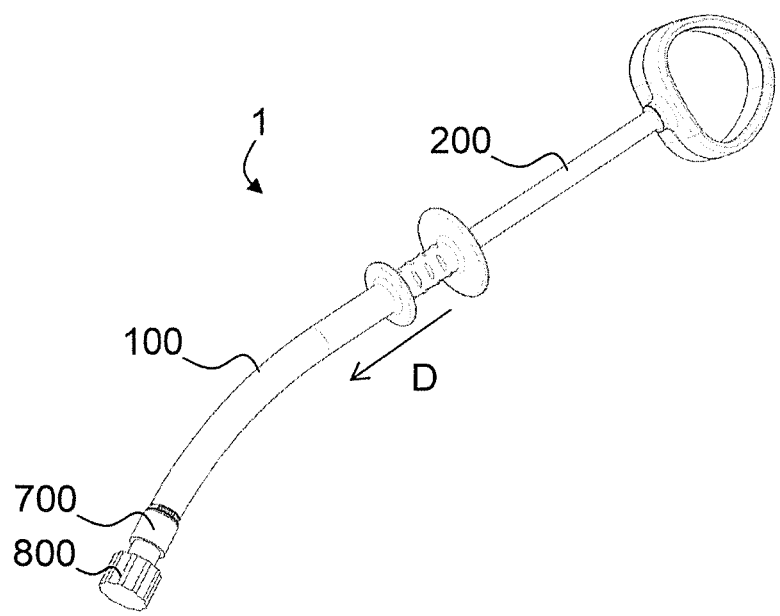
FIG. 36 shows a perspective view of a discharge device according to a sixth embodiment.
Figure 37:
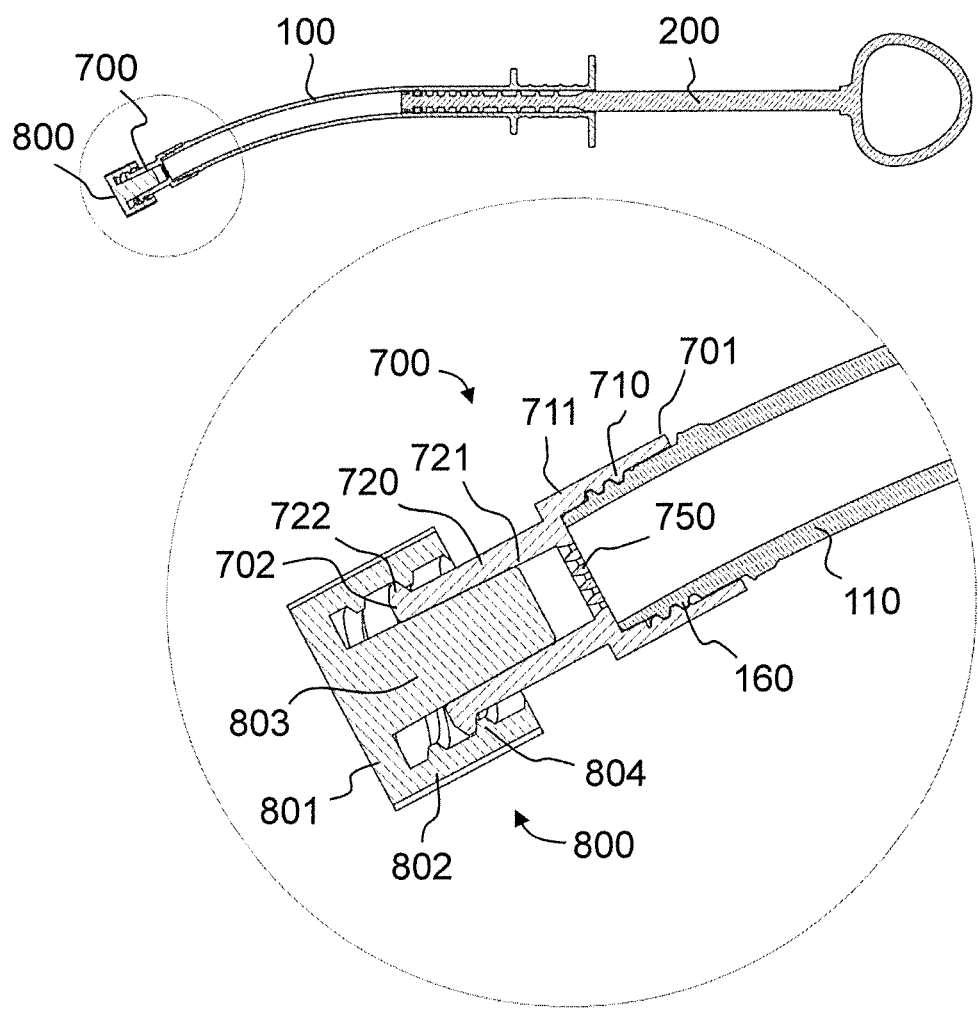
FIG. 37 shows a central longitudinal section through the discharge device of FIG. 36.
Figure 38:
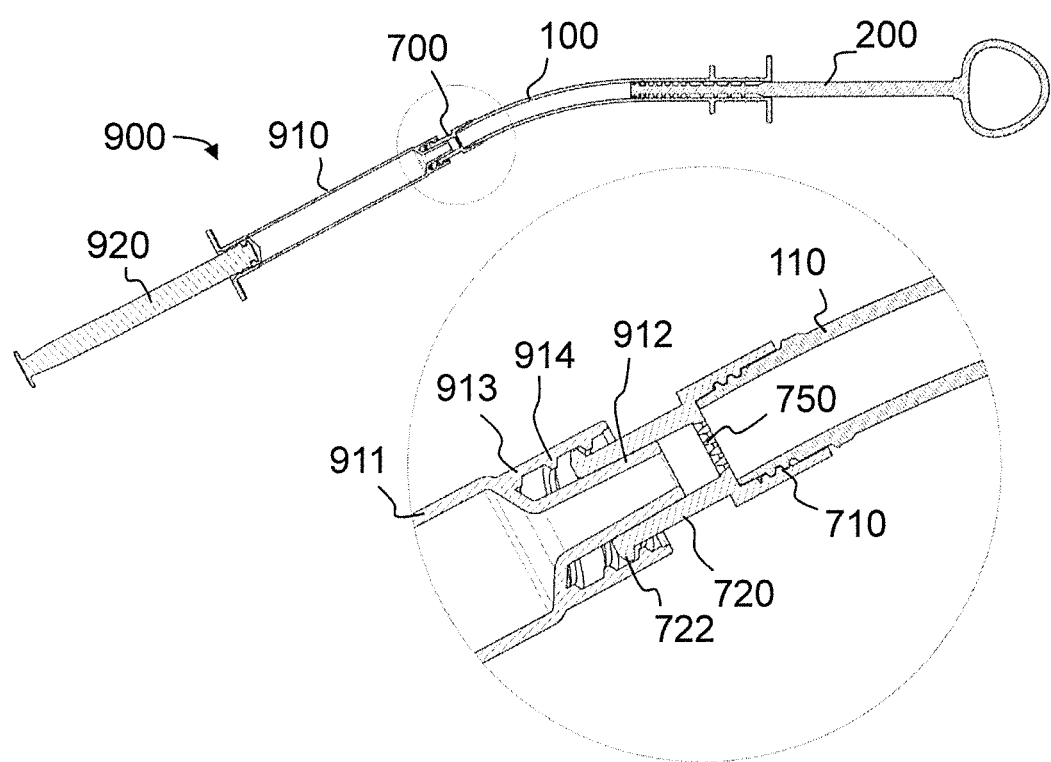
FIG. 38 shows a central longitudinal section through the discharge device of FIG. 36 in a state in which this discharge device has been connected to a commercially available syringe.

In FIGS. 36 to 38 a sixth exemplary embodiment of a discharge device 1 is illustrated. A separator element 700, which is specifically designed to be connected to a commercially available syringe in order to receive liquid from such a syringe into the container 100, is present in this exemplary embodiment.

The discharge device 1 in turn comprises a container 100 in which a feed element 200 is displaceably arranged. The aforementioned separator element 700 is attached via the distal end of the container 100. The separator element 700 has a filter region 750 with a plurality of filter openings, wherein the filter region 750 bears against the distal container end. A peripheral outer wall 711 with an internal thread 710 is configured proximally from the filter region 750. The internal thread 710 is in engagement with an external thread 160 on the container in the region of the distal end thereof. A connecting region 720 is configured distally from the filter region 750, said connecting region forming a female Luer taper 721. Two engagement elements 722 in the form of two short segments of an external thread are configured at the free distal end of the connecting region 720 on the outer face.

A closure 800 is screwed onto the separator element 700. The closure 800 has a top wall 801 and a peripheral outer wall 802. Starting from the top wall a plug 803 extends in the proximal direction. The plug forms a male Luer taper. An internal thread 804 is configured on the outer wall 802 on the inner face, said internal thread being in engagement with the engagement elements 722 of the separator element 700.

In order to wet the granulate received in the container 100 with liquid, initially the closure 800 is removed from the separator element 700. Then a commercially available syringe 900 is connected by the separator element 700 to a fluid reservoir 910 in which a piston 920 is displaceable (see FIG. 38). The fluid reservoir 910 of the syringe 900 has an outer wall 911 which forms a defining wall for the fluid reservoir 910 and an outlet region 912 adjoins the distal end thereof. The outlet region 912 forms on the outer face a male Luer taper. The outlet region is radially surrounded by a fastening ring 913 rigidly connected to the outer wall 911, an internal thread 914 being configured thereon. The fluid reservoir 910 is connected to the separator element 700 by the outlet region 912 being inserted into the connecting region 720 of the separator element 700 and then by being brought into engagement with the engagement elements 722 by a relative rotation of the internal thread 914 in the fastening ring 913. As a result, the syringe 900 is locked to the separator element 700.

Now the feed element 200 of the discharge device may be pulled back and/or the piston 920 advanced in the syringe 900, in order to transfer liquid from the reservoir 910 of the syringe into the container 100 of the discharge device. As a result, granulate received in the container 100 is wetted with the liquid.

In order to discharge the product thus obtained, the syringe 900 and the separator element 700 are removed from the container 100 and the product may then be discharged through the now open distal end of the container 100.

From the above description it is clear that a plurality of modifications is possible and the invention is not limited to the above-described exemplary embodiments.

LIST OF REFERENCE SIGNS

1 Discharge device
100 Container
101 Proximal container end
102 Distal container end
103 Insertion opening 104 Discharge opening
110 Container wall
120 Container interior
130 First finger support
140 Second finger support
150 Groove structure
160 External thread
170 Axial locking structure
180 Bridging structure
190 Rotational locking structure
200 Feed element
210 Piston rod
211 Guide bead
212 Distal region
220 Piston
230 Thumb ring
300 Separator element
301 Proximal end
302 Distal end
310 Internal thread
311 Outer wall region
312 Outer surface
320 External thread
321 Pipe connector
322 Cavity
330 Locking arm
331 Outer surface
332 Rear-engagement element
340 Driver element
350 Filter region
351 Through-opening
360 Engagement structure
400 Closure
401 Proximal end
402 Distal end
403 Proximal portion
404 Distal portion
410 Outer wall
420 Top wall
421 Plug
422 Proximal front face
423 Distal front face
430 Internal thread
440 Driver
450 Longitudinal rib
460 Intermediate space
470 Second internal thread
500 Closure
510 Outer wall
520 Top wall
530 Internal thread
600 Packaging
610 Carrier
620 Receiver recess
621-626 Recess regions
630 Closure holding recess
631 Marking
640 Fluid reservoir recess
641 Marking
700 Separator element
701 Proximal end
702 Distal end
710 Internal thread
711 Outer wall
720 Connecting region
721 Female Luer taper
722 Engagement element
750 Filter region
800 Closure
801 Top wall
802 Outer wall
803 Plug
804 Internal thread
900 Syringe
910 Reservoir
911 Outer wall
912 Outlet region
913 Fastening ring
914 Internal thread
920 Piston
L Central longitudinal axis
D Distal direction
P Proximal direction
$R_{max}$ Maximum radius
α Angle of curvature

The invention claimed is:

1. A separator element with a proximal end and a distal end, comprising:
a filter region which is configured to prevent the passage of a granulate in an axial direction between the proximal end and the distal end but to permit the passage of liquid in the axial direction; and an external thread which is open toward the distal end and which extends around the axial direction; an internal thread which is open toward the proximal end and which extends around the axial direction; wherein at least one of:
i) at least one resilient locking arm is arranged on the outer periphery, which is configured in the region of the proximal end and which extends with its free end toward the proximal end, and ii) the separator element comprises one or more driver elements which are configured on the outer face on the separator element in order to permit a positive engagement of the separator element with a driver of a closure in the peripheral direction.

2. The separator element as claimed in claim 1, wherein the at least one locking arm has a rear-engagement element in the region of its free end on the inner face.

3. The separator element as claimed in claim 1, wherein the at least one locking arm in the region of its free end on the inner face has an engagement structure which is configured to cooperate with a rotational locking structure on a container.

4. The separator element as claimed in claim 1, wherein the at least one locking arm is configured on the outer periphery on the separator element such that an outer surface of the at least one locking arm is arranged flush with an outer surface of the separator element located distally from the locking arm, or is arranged offset radially outwardly.

5. The separator element as claimed in claim 1, wherein the at least one locking arm extends as far as a region located proximally from the internal thread in the axial direction.

6. The separator element as claimed in claim 1, wherein the driver elements form a toothing in the peripheral direction.

7. The separator element as claimed in claim 1, wherein the external thread is configured on a pipe connector which defines a cavity on the inside, wherein the cavity is delimited in the proximal direction by the filter region.

8. The separator element as claimed in claim 1,
wherein the separator element has a connecting region which is located distally from the filter region and which forms a female Luer taper which is open toward the distal end.

9. The separator element as claimed in claim 8, wherein the connecting region on the outer face has an engagement element for an internal thread of an attachment.

10. A discharge device comprising: a separator element with a proximal end and a distal end; and a container for receiving a product with a peripheral container wall, a proximal container end, a distal container end and a discharge opening on the distal container end, wherein an external thread which extends around the axial direction is configured on the container wall in the region of the distal container end, wherein the separator element comprises a filter region which is configured to prevent the passage of a granulate in an axial direction between the proximal end and the distal end but to permit the passage of liquid in the axial direction, and an external thread which is open toward the distal end and which extends around the axial direction; an internal thread which is open toward the proximal end and which extends around the axial direction, wherein at least one of: i) at least one resilient locking arm is arranged on the outer periphery, which is configured in the region of the proximal end and which extends with its free end toward the proximal end, and ii) the separator element comprises one or more driver elements which are configured on the outer face on the separator element in order to permit a positive engagement of the separator element with a driver of a closure in the peripheral direction, and wherein the external thread of the container is able to be brought into engagement with the internal thread of the separator element in order to attach the separator element to the distal container end.

11. The discharge device as claimed in claim 10,
wherein an axial locking structure is configured proximally from the external thread of the container on the outer face on the container wall, and
wherein the at least one locking arm of the separator element is able to be brought into engagement with the axial locking structure, such that a proximal movement of the separator element relative to the container is impeded, and is able to be brought out of engagement by an outward radial deflection of the locking arm.

12. The discharge device as claimed in claim 11, wherein the axial locking structure comprises an annular bead, the at least one locking arm being able to be brought thereby into locking engagement in a resilient manner.

13. The discharge device as claimed in claim 10,
wherein a rotational locking structure is configured proximally from the external thread of the container on the outer face on the container wall, and
wherein a complementary engagement structure is configured on the inner face on at least one locking arm of the separator element, said complementary engagement structure being able to be brought into engagement with the rotational locking structure, such that it impedes a rotation of the separator element relative to the container, and being able to be brought out of engagement by an outward radial deflection of the locking arm.

14. The discharge device as claimed in claim 13,
wherein the rotational locking structure is configured as an external toothing which extends at least over a part of the periphery of the container wall, and/or
wherein the complementary engagement structure is configured as an internal toothing.

15. The discharge device as claimed in claim 10,
wherein the container has a first finger support on the outer face at the proximal container end, and
wherein the container has a second finger support distally from the finger support on the outer face, so that the fingers of a user are impeded from slipping in a distal direction.

16. The discharge device as claimed in claim 10, comprising a closure with a peripheral outer wall, a proximal closure end, a distal closure end and a top wall,
wherein the top wall of the closure axially covers the distal end of the separator element in the closing position, and
wherein the outer wall radially covers the at least one locking arm in the closing position such that the outer wall impedes a radial deflection of the locking arm.

17. The discharge device as claimed in claim 16, wherein the outer wall of the closure in the closing position extends in the proximal direction at least as far as the proximal end of the separator element so that the closure entirely covers the separator element in the closing position.

18. The discharge device as claimed in claim 16,
wherein an internal thread which is open toward the proximal closure end and which extends around the axial direction is configured in the outer wall of the closure,
wherein the separator element comprises an external thread which is open toward the distal end and which extends around the axial direction, and
wherein in the closing position the external thread of the separator element is in engagement with the internal thread of the closure.

19. The discharge device as claimed in claim 18, wherein the external thread of the separator element and the external thread of the container are of the same dimensions so that the closure optionally may be screwed with its internal thread onto the separator element or directly onto the container.

20. The discharge device as claimed in claim 18,
wherein the external thread of the separator element is configured on a pipe connector which defines a cavity on the inside, wherein the cavity is delimitted in the proximal direction by the filter region, and
wherein the closure has a plug which is configured on the top wall of the closure, wherein the plug extends in the interior of the closure in the direction of the proximal closure end and extends in the closing position into the cavity.

21. The discharge device as claimed in claim 20,
wherein the top wall defines a distal front face,
wherein between the distal front face and the distal closure end the closure has a second internal thread which is open toward the distal closure end, which extends around the axial direction and which is configured in a complementary manner to the external thread on the distal container end, and
wherein the closure is able to be screwed with the second internal thread in a reverse orientation relative to the closing position onto the external thread at the distal container end such that the distal front face covers the distal container end.

22. The discharge device as claimed in claim 16,
wherein the outer wall of the closure has one or more drivers distally from the top wall on the inner face,
wherein the separator element has one or more driver elements on the outer face, and
wherein the drivers are able to be brought into engagement with the driver elements of the separator element by the closure being connected to the separator element in a reverse orientation relative to the closing position in the axial direction so that the separator element is able to be unscrewed from the container by means of the closure.

23. The discharge device as claimed in claim 10 further comprising:
- a closure with a peripheral outer wall, a proximal closure end, a distal closure end and a top wall,
- wherein the closure is able to be attached to the separator element in a closing position, such that the top wall of the closure axially covers the distal end of the separator element,
- wherein the outer wall of the closure has one or more drivers distally from the top wall on the inner face, and
- wherein the drivers are able to be brought into engagement with the driver elements of the separator element by the closure being connected to the separator element in a reverse orientation relative to the closing position in the axial direction so that the separator element is able to be unscrewed from the container by means of the closure.

24. The discharge device as claimed in claim 10, wherein the separator element has a connecting region which is located distally from the filter region and which forms a female Luer taper which is open toward the distal end,
- the discharge device further comprising a closure which has a top wall, an outer wall, a male Luer taper extending from the top wall in a proximal direction as well as an internal thread configured on the outer wall proximally from the top wall, wherein the internal thread is able to be brought into engagement with an engagement element configured on the outer face on the connecting region of the separator element.

* * * * *